United States Patent [19]
Lovato et al.

[11] Patent Number: 6,024,751
[45] Date of Patent: Feb. 15, 2000

[54] METHOD AND APPARATUS FOR TRANSURETHRAL RESECTION OF THE PROSTATE

[75] Inventors: Paul H. Lovato, Sunnyvale; David Alan Gollnick, Redwood City; Russell Alex Zinner, Mountain View; David P. Thompson, San Jose; Kevin Connors; Michael Hmelar, both of Palo Alto, all of Calif.

[73] Assignee: Coherent Inc., Santa Clara, Calif.

[21] Appl. No.: 08/837,003

[22] Filed: Apr. 11, 1997

[51] Int. Cl.⁷ .................................................. A61B 17/32

[52] U.S. Cl. ............................ 606/170; 604/22; 606/180

[58] Field of Search ............................... 606/1, 167, 170, 606/171, 180; 604/22

[56] References Cited

U.S. PATENT DOCUMENTS

| | | |
|---|---|---|
| 3,289,669 | 12/1966 | Dwyer et al. . |
| 4,246,902 | 1/1981 | Martinez . |
| 4,436,097 | 3/1984 | Banko . |
| 4,620,547 | 11/1986 | Boebel . |
| 4,657,018 | 4/1987 | Hakky . |
| 4,846,192 | 7/1989 | MacDonald . |
| 4,909,782 | 3/1990 | Semm et al. . |
| 4,955,882 | 9/1990 | Hakky . |
| 5,106,364 | 4/1992 | Hayafuji et al. . |
| 5,201,731 | 4/1993 | Hakky . |

(List continued on next page.)

FOREIGN PATENT DOCUMENTS

| | | |
|---|---|---|
| 0 185 810 | 2/1986 | European Pat. Off. . |
| 0 310 285 | 5/1989 | European Pat. Off. . |
| 9304869 | 4/1993 | Germany . |
| 1116465 | 6/1968 | United Kingdom . |
| WO 96/32895 | 10/1996 | WIPO . |

OTHER PUBLICATIONS

Arthroscopic Blades and Burrs, Zimmer information brochure, 1996, 7 pages.
Prof. Dr. Dr. H.C. Mult. Kurt Semm, F.R.C.O.G. (ED.), F.I.C.S. (HON.), "Tissue Morcellation In Endoscopic Surgery", Surgical Technology International V, International Developments In Surgery & Surgical Research, (1996), pp. 175–178.
Anthrex, Inc. "Adapteur Power System (APS)", 1996.
Anthrex, Inc. "Single Use Shaver Blades and Burs", 1996.
WISAP, "Macro–Morcellation—10, 15, and 20 mm. Diamter Now With Moto–Drive", 1996.
Smith & Nephew, Inc. "Shaver Systems–Endoscopic Powered Instrument System", 3 pages, Mar., 1997.

Primary Examiner—Michael Buiz
Assistant Examiner—William Lewis
Attorney, Agent, or Firm—Limbach & Limbach L.L.P.

[57] ABSTRACT

A method and apparatus for transurethral resection of the prostate, which includes inserting a transurethral incisional device through the patient's urethra, incising off at least one piece of targeted prostatic tissue using the incisional device, inserting a morcellation probe through the patient's urethra, morcellating the excised piece of targeted prostatic tissue with the morcellation probe, and aspirating the morcellated prostatic tissue through the morcellation probe and out of the patient.

The morcellation probe of the present invention includes an elongated inner probe tube that defines an aspiration channel therein. The inner probe tube is slidably disposed inside an outer probe tube. The outer probe tube has a first aperture with a first cutting edge for cutting tissue. The inner probe tube has a second aperture or a spiral shaped groove defining a second cutting edge that moves relative to the first cutting edge to cut tissue drawn through the first aperture. The second aperture or groove are in communication with the aspiration channel. A tissue manipulation port can be formed in either the outer or inner probe tubes to overlap with the inner or outer probe tube apertures or the groove to provide continuous aspiration adjacent the first aperture if/when the first aperture is sealed by the inner probe tube.

47 Claims, 16 Drawing Sheets

U.S. PATENT DOCUMENTS

| | | |
|---|---|---|
| 5,242,460 | 9/1993 | Klein et al. . |
| 5,312,399 | 5/1994 | Hakky et al. . |
| 5,370,651 | 12/1994 | Summers . |
| 5,403,276 | 4/1995 | Schechter et al. . |
| 5,456,689 | 10/1995 | Kresh et al. ............................ 606/180 |
| 5,458,112 | 10/1995 | Weaver . |
| 5,490,860 | 2/1996 | Middle et al. . |
| 5,498,258 | 3/1996 | Hakky et al. ............................ 606/170 |
| 5,527,332 | 6/1996 | Clement . |
| 5,569,284 | 10/1996 | Young et al. ............................ 606/170 |
| 5,733,297 | 3/1998 | Wang . |

METHOD AND APPARATUS FOR TRANSURETHRAL RESECTION OF THE PROSTATE

FIELD OF THE INVENTION

The present invention relates to prostate resection, and in particular to a method and apparatus for transurethral resection of prostatic tissue.

BACKGROUND OF THE INVENTION

The prostate is a male reproductive system gland that is generally made of three lobes that are enclosed by an outer layer of tissue referred to as the capsule. The prostate surrounds the lower portion of the bladder (where urine is stored) and part of the urethra (the canal through which urine passes from the bladder out of the body).

Continued growth of the prostate causes Benign Prostatic Hypertrophy (BPH), where the continually growing prostate tissue squeezes the lower portion of the bladder and the urethra, making it difficult to pass urine.

BPH is often treated by surgically removing the excess prostatic tissue from the interior region of the prostate that is pressing on the urethra, which usually relieves the obstruction and the incomplete emptying of the bladder caused by the BPH, leaving the rest of the prostatic tissue and the capsule intact.

Surgeons often perform transurethral surgery to remove the excess prostate tissue (targeted prostatic tissue). This surgery is performed by inserting a resectoscope through the urethra. The resectoscope is used to view the interior of the urinary tract, and to cut (incise) off pieces of the targeted prostatic tissue. Following surgery, a urinary catheter is inserted into the urethra to drain urine from the bladder. This catheter is usually left in place until the presence of blood in the urine has diminished, usually within 1–4 days.

There are several prostate resection procedures currently being used. The TURP procedure (transurethral resection of the prostate) is a very common treatment of BPH. During a TURP procedure, the surgeon uses a standard electrosurgical cutting loop to remove the obstructing tissue from the prostate. The electrosurgical cutting loop is inserted through the resectoscope to the targeted prostatic tissue. The electrosurgical cutting loop uses electricity to "shave" off small pieces of the targeted prostate tissue from the interior of the prostate. During surgery, the shaved pieces of prostatic tissue are carried by irrigation fluid flowing through the resectoscope into the bladder. At the end of the operation, these pieces of excised prostatic tissue are flushed out of the bladder using irrigant, aspirated out using a large bore syringe, and/or removed through the resectoscope using a grasping device.

The pieces of prostatic tissue excised by the electrosurgical loop must be small enough to flush out with the irrigant, aspirate out using the large bore syringe, or grasped and removed through the resectoscope. Therefore, the surgeon must make many surgical incisions into the targeted prostatic tissue with the electrosurgical cutting loop, each of which resulting in the extraction of a piece of prostatic tissue having limited size and significant bleeding. The more surgical incisions made by the surgeon with the electrosurgical loop, the more opportunity for error. In addition, because there is a high number of excised pieces of prostatic tissue to be removed from the bladder, the flushing, aspiration, and/or grasping methods of tissue removal can be time consuming.

There are also thermotherapy techniques that cook the prostatic tissue to reduce the size of the enlarged prostatic tissue. For example, VLAP (visual laser ablation of the prostate) employs an Nd:Yag laser to irradiate and heat each of the prostatic lobes from within the urethra at a given power for a given time duration. Interstitial thermotherapy uses an Nd:Yag laser and/or microwave energy and injects heat into the lateral lobes of the prostate. Within two months of treatment the affected tissue dies and the cells stuff off and eventually flush out of the patient through their urine. If the laser is used, the laser energy coagulates the treated tissue which limits bleeding and preserves a clearer field of view for the surgeon. Tissue removal using thermotherapy techniques is inefficient, as it takes several months to fully clear the dead tissue from the patient's system. The patient can be catheterized for up to two weeks because of excessive swelling of the prostatic tissue. Also, these procedures are not very precise. It is difficult to control the thermal end point of the affected tissue, and hence difficult to control the extent of ultimate tissue necrosis. There is also no visual indication as to what tissue has been sufficiently heated, and to what depth. Lastly, the dead tissue being flushed out over a long period of time invites infection and causes prolonged irritative symptoms for the patient.

New procedures have been developed with the commercialization of laser systems that exhibit low penetration depths in tissue. For example, erbium (wavelength=2.94 or 2.71 um) and holmium (wavelength=2.1 um) laser systems produce optical outputs that penetrate only a few hundred microns in an aqueous environment. Therefore, side and end firing optical fibers can be inserted through the resectoscope to incise and ablate the prostatic tissue. The laser energy vaporizes the water content of cells and coagulates the underlying tissue, thus significantly reducing the bleeding and swelling that otherwise results from TURP and VLAP, as well as reducing the amount of catheterization time during recovery, while providing immediate relief of the BPH symptoms.

The tissue ablation rate of such laser systems is far too low to simply use a side or end firing fiber to ablate away all the targeted prostatic tissue. However, holmium and erbium lasers have been used to incise a urination channel in the urethra after a thermotherapy procedure. The urination channel allows for an earlier removal of the catheter.

The HoLRP procedure (holmium laser resection of the prostate), has recently been developed, and uses laser light from a holmium laser system to remove the targeted prostatic tissue. The laser light is transmitted through an optical fiber inserted through the resectoscope to the targeted prostatic tissue. The laser light cuts the excess tissue from the interior of the prostate in much the same way as the electrosurgical loop in TURP, while coagulating the underlying tissue. The excised pieces of prostatic tissue are carried by irrigation fluid flowing through the resectoscope into the bladder. At the end of the operation, these pieces of excised prostatic tissue are flushed, aspirated, or grasped and removed from the bladder (and/or from the urethra (fossa)) in the same manner as the TURP procedure. As discussed above, these pieces of excised prostatic tissue must be of limited size, for removal by irrigation, large bore syringes and/or grasping tools, which can be a time consuming procedure. Further, the surgeon makes as many as 50 to 60 incisions per procedure in order to limit the size of the excised pieces of prostatic tissue, thus increasing the risk of inadvertent damage to surrounding tissue.

All of the above procedures suffer from the limitation that the excised pieces of prostatic tissue must be small enough for removal from the bladder. This limitation requires additional surgeon skill and time in incising the targeted prostatic tissue into small pieces, and more additional time removing all the excised pieces of tissue from the bladder. Prolonging the prostate resection procedure is costly in that it ties up operating room time, and requires the patient to be anesthetized longer thus increasing the risks of this surgical procedure. There is a need for a transurethral prostatic tissue removal method and device that accurately, efficiently and safely incises and removes targeted prostatic tissue from the patient. Ideally, such a method and device would minimize the number of incisions performed by the surgeon, and reduce the time necessary to extract all the excised pieces of tissue from the patient, thus reducing the time the operating room is occupied and the patient is anesthetized.

SUMMARY OF THE INVENTION

The present invention is an improved method and apparatus for transurethral prostate resection. The method and apparatus simplify the resection of prostatic tissue by minimizing the number of the incisions made into the targeted prostatic tissue, and simplifying the removal process of the excised pieces of tissue by using a morcellation probe.

The method of the present invention includes inserting a transurethral incisional device through the patient's urethra, incising off at least one piece of targeted prostatic tissue using the incisional device, inserting a morcellation probe through the patient's urethra, morcellating the excised piece of targeted prostatic tissue with the morcellation probe, and aspirating the morcellated prostatic tissue through the morcellation probe and out of the patient.

In one aspect of the present invention, the morcellation probe of the present invention includes an elongated outer probe tube defining a first interior channel therein and having a longitudinal axis and a first aperture formed adjacent to a closed distal end of the outer probe tube. An elongated inner probe tube defining an aspiration channel therein has a longitudinal axis and a second aperture formed adjacent to a distal end thereof. The inner probe tube is slidably disposed inside the first interior channel. A proximate end of the inner probe tube is connectable to a vacuum source. The inner probe tube is movable relative to the outer probe tube between a first position, where the first and second apertures at least partially overlap each other, and a second position, where the first and second apertures do not overlap each other.

A tissue manipulation port is formed in either the outer probe tube adjacent the first aperture, or the inner probe tube adjacent the second aperture. The tissue manipulation port at least partially overlaps one of the first and second apertures when the inner probe tube is in the second position.

The first aperture has a first cutting edge and the second aperture has a second cutting edge. The first and second cutting edges pass each other when the inner probe tube moves from the first position to the second position.

During operation, aspiration caused by a vacuum in the aspiration channel from the vacuum source manipulates the targeted tissue to the first aperture and draws a portion of the targeted tissue into the first and second apertures when the inner probe tube is in the first position. The portion of targeted tissue is cut by the first and second cutting edges passing each other when the inner probe tube moves from the first position to the second position. The cut portion of targeted tissue is drawn into and through the aspiration channel. The tissue manipulation port provides suction from the aspiration channel to hold the target tissue in position while the inner probe tube is in the second position.

In another aspect of the present invention, the first aperture has opposing first and second cutting edges, and the second aperture has opposing third and fourth cutting edges. The inner probe tube is movable relative to the outer probe tube between a first position, a second position, and a medial position which is between the first and second positions. The first and second apertures at least partially overlap each other when the inner probe tube is in the medial position. The first and second apertures do not overlap each other when the inner probe tube is in either of the first and second positions.

A first tissue manipulation port is formed adjacent to one of the first and third cutting edges, and overlaps with one of the first and second apertures when the inner probe tube is in the first position. A second tissue manipulation port is formed adjacent to one of the second and fourth cutting edges, and overlaps with one of the first and second apertures when the inner probe tube is in the second position.

During operation, aspiration caused by a vacuum in the aspiration channel from the vacuum source manipulates the targeted tissue to the first aperture and draws a portion of the targeted tissue into the first and second apertures when the inner probe tube is in the medial position. The portion of targeted tissue is cut by the first and third cutting edges passing each other when inner tube moves from the medial position to the first position, and by the second and fourth cutting edges passing each other when the inner tube moves from the medial position to the second position. The cut targeted tissue is drawn into and through the aspiration channel. The first and second tissue manipulation ports provide suction from the aspiration channel to hold the target tissue in position while the inner probe tube is in the first and second positions.

In yet another aspect of the present invention, the morcellation probe includes an elongated outer probe tube defining a first interior channel therein, and has a longitudinal axis and a first aperture formed adjacent to a closed distal end thereof.

An elongated inner probe tube defines an aspiration channel therein, and has a longitudinal axis and an outer surface. A spiral shaped groove is formed in the outer surface. An aspiration port, in communication with the aspiration channel, is formed in the groove. The inner probe tube is slidably disposed inside the first interior channel and rotatable about its longitudinal axis relative to the outer probe tube. A proximate end of the inner probe tube is connectable to a vacuum source.

The first aperture has a first cutting edge and the groove defines a spiral shaped second cutting edge. The first and second cutting edges pass each other when the inner probe rotates relative to the outer probe tube.

During operation, aspiration caused by a vacuum in the aspiration channel from the vacuum source manipulates the targeted tissue to the first aperture and draws a portion of the targeted tissue into the first aperture and the groove. The portion of targeted tissue is cut by the first and second cutting edges passing each other when the inner probe tube is rotated relative to the outer probe tube. The cut portion of targeted tissue is drawn along the groove, through the aspiration port and through the aspiration channel. Alternately, a vacuum source is connected to provide a vacuum in a space between the inner and the outer probe tubes, where aspiration caused by the vacuum in the space from the vacuum source manipulates the targeted tissue to the first aperture and draws a portion of the targeted tissue into the first aperture and the groove, and the portion of targeted tissue is cut by the first and second cutting edges passing each other when the inner probe tube is rotated relative to the outer probe tube. The cut portion of targeted tissue is drawn along the groove and the space to the vacuum source.

Other aspects and features of the present invention will become apparent by a review of the specification, claims and appended figures.

DETAILED DESCRIPTION OF THE PREFERRED EMBODIMENTS

The present invention is a method and apparatus for transurethral resection of the prostate, which includes incising off pieces of targeted prostatic tissue, and morcellating the excised pieces of prostatic tissue for aspiration out of the patient.

Figure 1A:
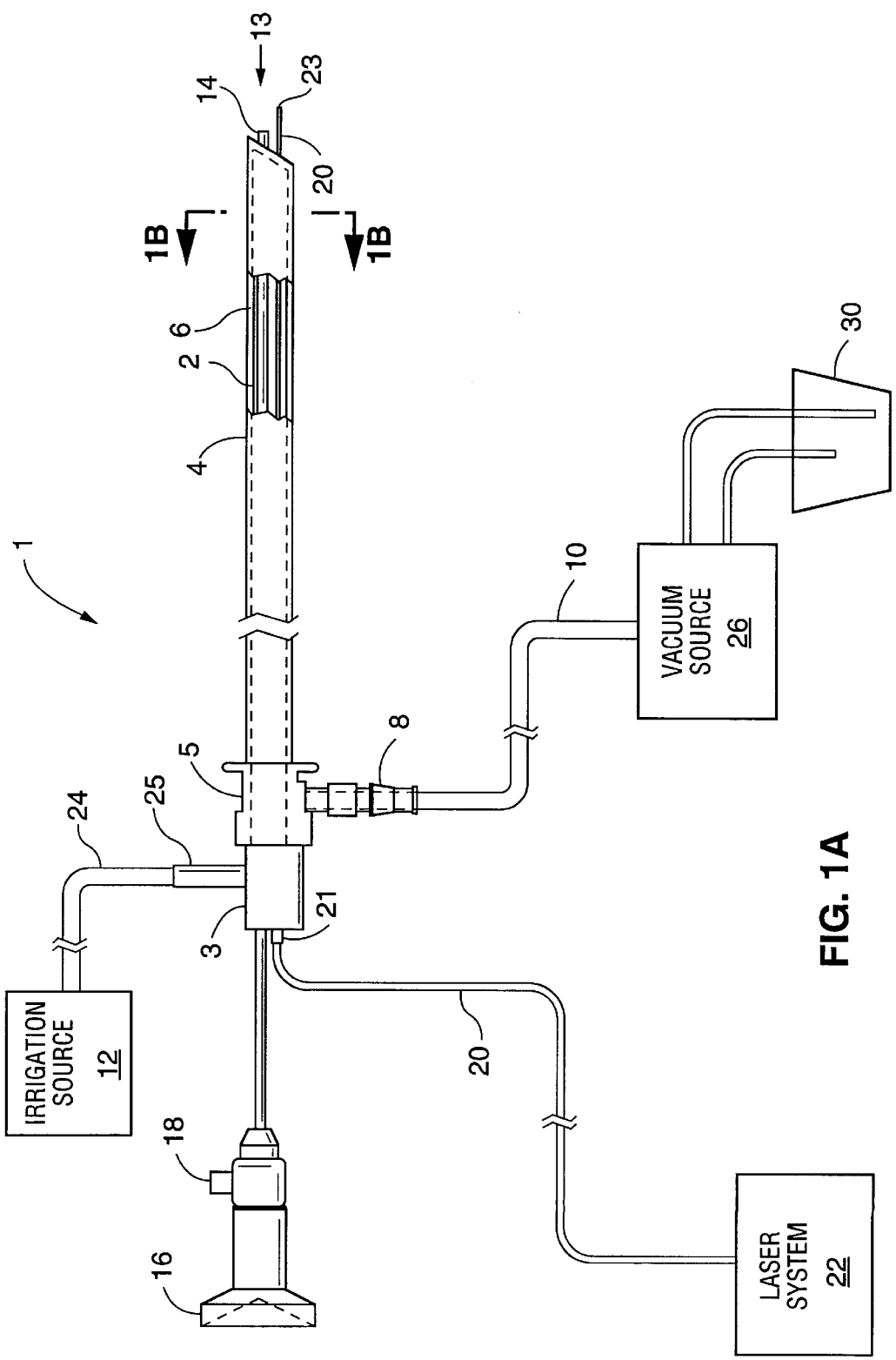
FIG. 1A is a side view of the transurethral resectoscope with an optical fiber.
Figure 1B:
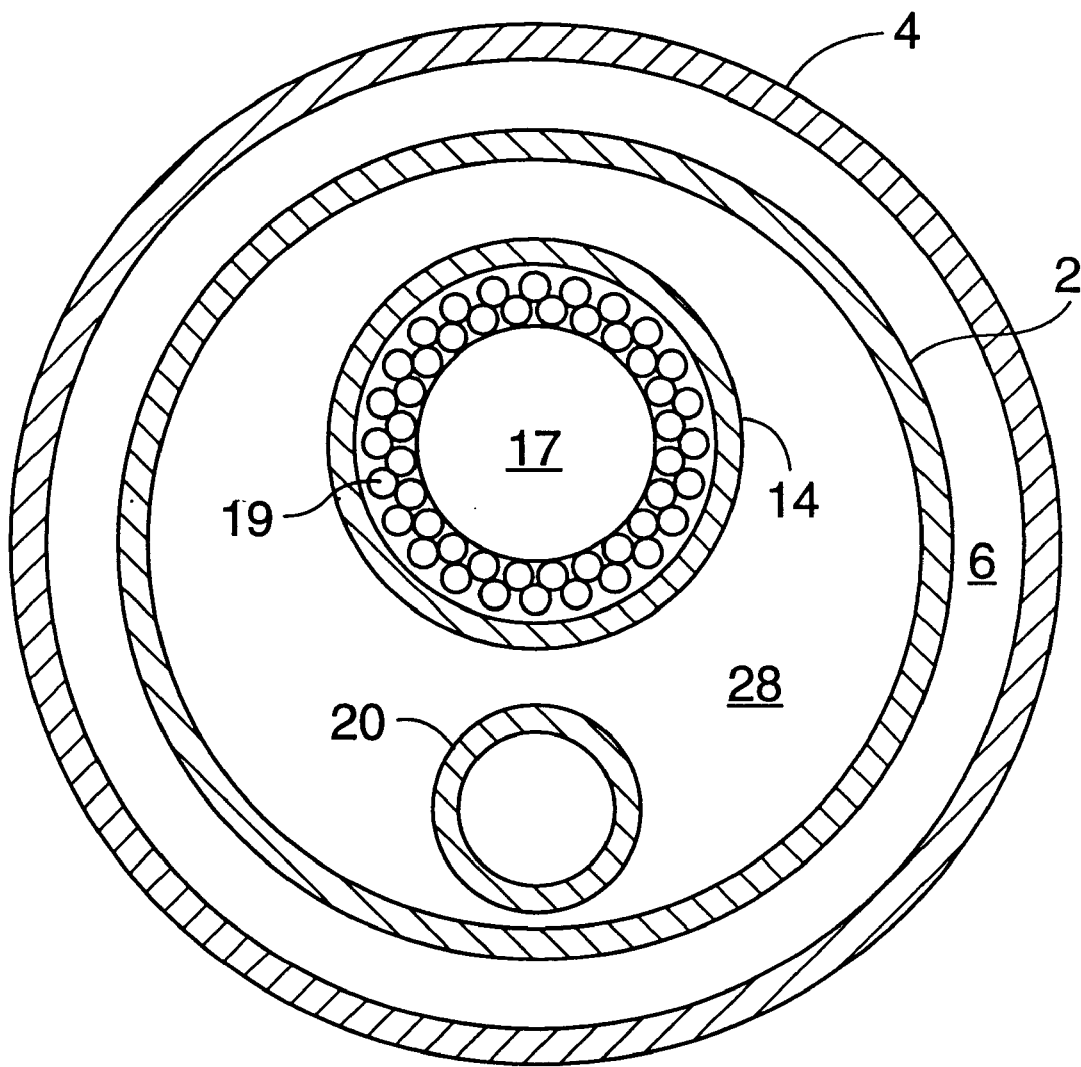
FIG. 1B is a cross-sectional end view of the transurethral resectoscope with an optical fiber.

In the preferred embodiment, the incising step is performed using optical energy delivered by a transurethral resectoscope 1 as shown in FIGS. 1A and 1B. Resectoscope 1 includes an inner sheath 2 surrounded by an outer sheath 4, with an aspiration channel 6 formed therebetween. A port 8 is located at the proximate end 5 of outer sheath 4, and is connected to an aspiration line 10 that connects to a vacuum source 26. The vacuum source 26 is a mechanical pump capable of creating a variable vacuum, and with a tissue trap 30 to collect tissue and fluids aspirated from the patient. Alternately, the vacuum source 26 is a gravity drainage system that can provide a variable vacuum based upon its height below the resectoscope 1.

Inner sheath 2 forms an irrigation channel 28 therein that terminates with irrigation port 25. Irrigation line 24 connects to port 25 to an irrigation source 12, which provides suitable irrigation fluid through irrigation line 24, channel 28, and out the delivery end 13 of the outer sheath 4. The proximate end 3 of inner sheath 2 attaches to and forms a seal with proximate end 5 of outer sheath 4.

Figure 1C:
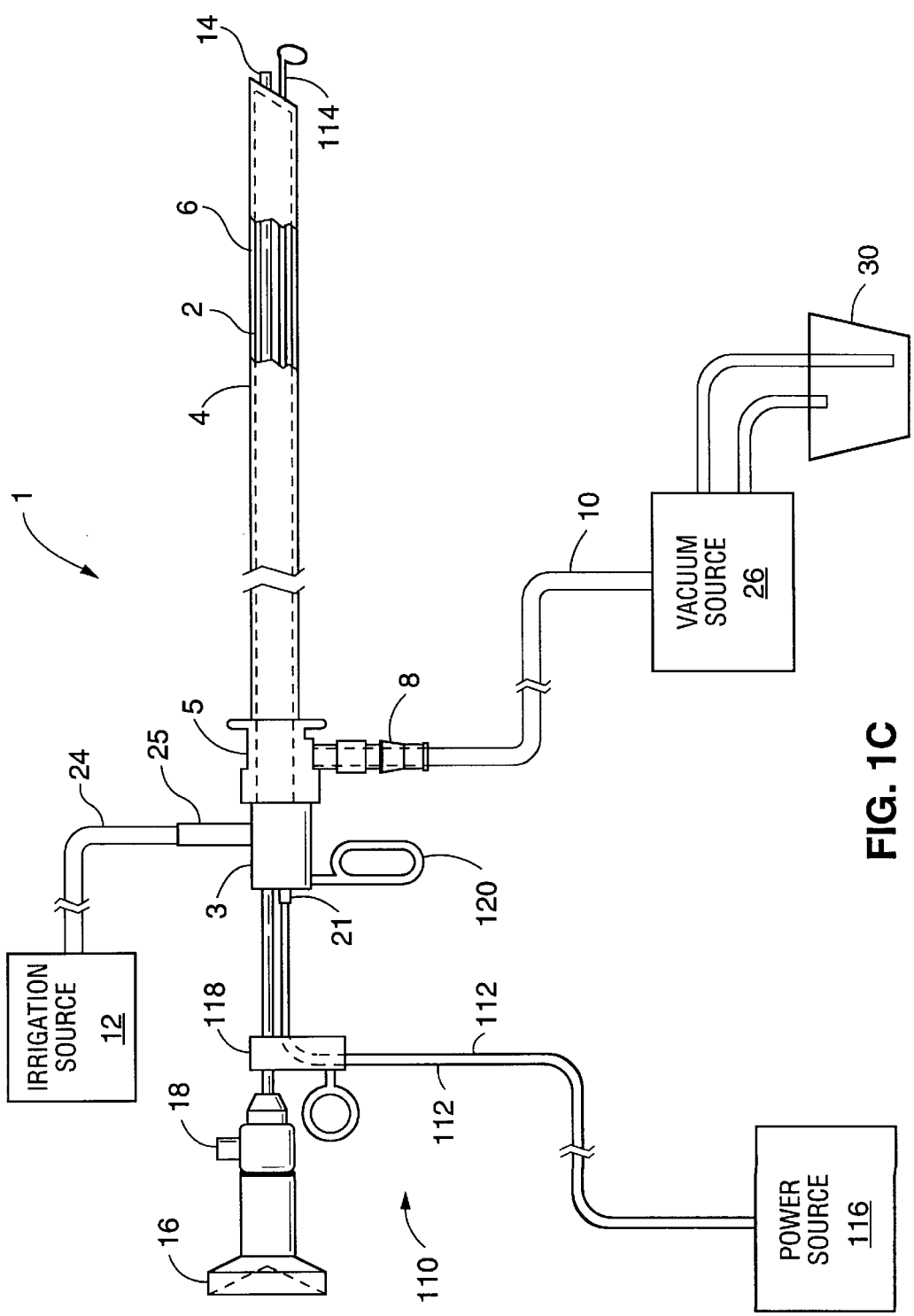
FIG. 1C is a side view of the transurethral resectoscope with an electrosurgical device.
Figure 1D:
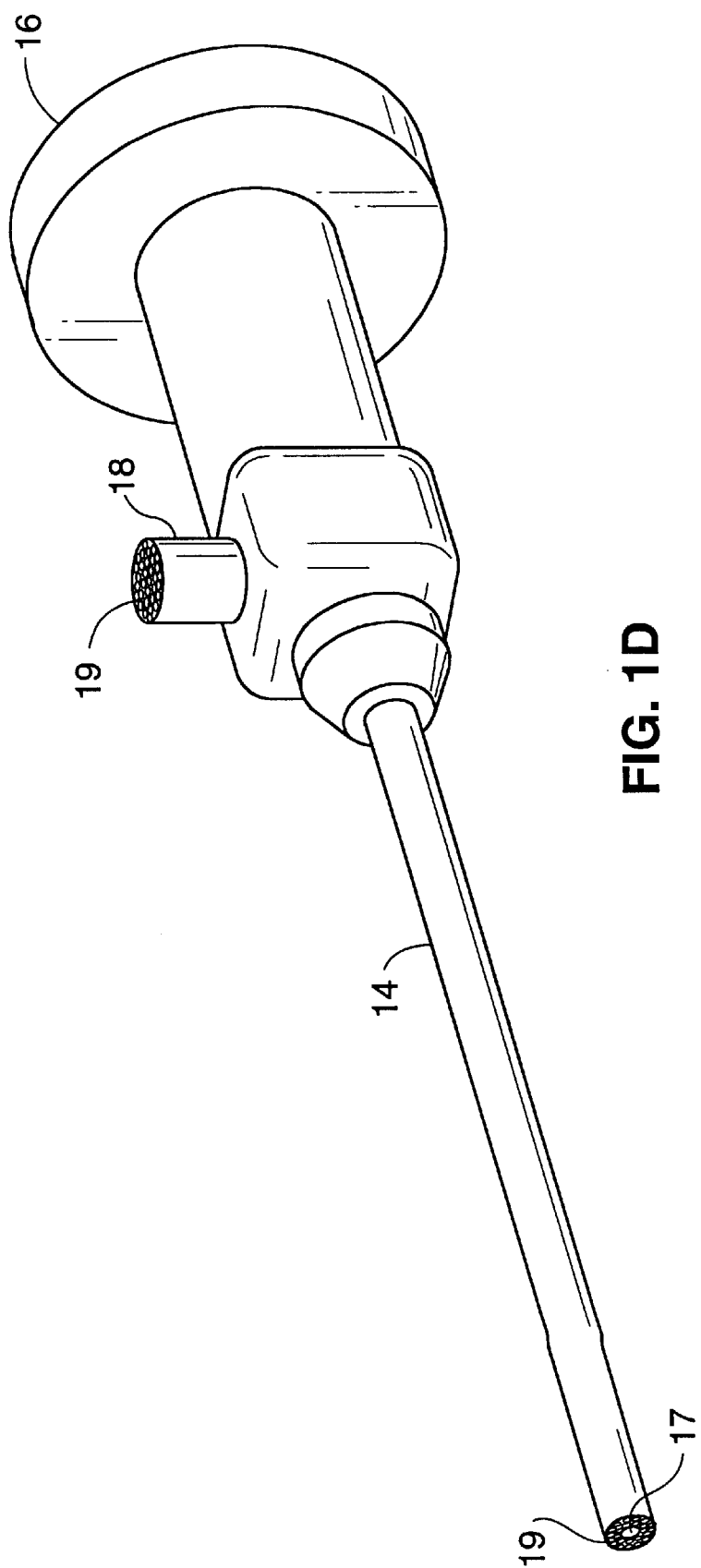
FIG. 1D is a perspective view of the telescope used with the transurethral resectoscope.

A telescope 14 includes a viewing channel 17 surrounded by a plurality of optical fibers 19, as best illustrated in FIG. 1D. The telescope 14 inserts through proximate end 3 and extends along the inside length of the inner sheath 2. The proximate end of telescope 14 includes an eyepiece 16 for viewing down the viewing channel 17, and an illumination port 18. The optical fibers 19 extend from illumination port 18, down the outside of viewing channel 17 and terminate at the distal end of telescope 14. A light source (not shown) connects to the illumination port 18 to illuminate the area beyond the distal end of telescope 14 via the optical fibers 19.

An optical fiber 20 is attached at one end to laser system 22. The fiber 20 extends through a input port 21, along the inside length of the inner sheath 2, and out the delivery end 13 of outer sheath 4. The delivery end 23 of optical fiber 20 can direct the laser energy out longitudinally (end firing fiber) or laterally (side firing fiber). The optical fiber 20 can be held in place by a wire loop, metal strap, or any equivalent thereof attached near the end, or along the length, of inner sheath 2.

The laser system 22 can be any laser system operating with a wavelength between approximately 200 nm and 3.0 um. Preferably, laser system 22 is a holmium laser that operates at 2.1 um, with 2–2.8 joules per pulse running at 25 Hz or higher. Alternately, laser system 22 could be an erbium laser system operating at 2.94 or 2.71 um, or an Nd:Yag laser operating at 1064 nm, or a doubled Nd:Yag laser system using, for example, a KTP doubling configuration operating at 532 nm.

Under the method of the present invention, the resectoscope 1 is inserted through the patient's urethra until the delivery end 13 is adjacent the targeted prostatic tissue. The irrigation source 12 and vacuum source 26 are activated to provide irrigation and aspiration (suction) at the delivery end 13. The combination of irrigation and aspiration maintains a clean environment for the procedure, and a clear field of view for the surgeon.

The surgeon, viewing through the eyepiece 16, positions the delivery end 23 of fiber 20 adjacent the tissue to be incised. Feeding the fiber 20 through input port 21 extends the delivery end 23 of fiber 20 further away from the delivery end 13 of outer sheath 4. The laser system 22 is activated and the targeted prostatic tissue is incised using the optical energy exiting the optical fiber 20. The targeted prostatic tissue can be incised and separated from the surgical capsule either in its entirety, or in relatively large pieces. It is preferable to incise the targeted prostatic tissue off in its entirety to minimize the number of incisions made during the procedure. Further, by making one continuous incision along the capsule (wall of the prostate), it is much easier to visualize and incise along the margin between the prostatic tissue to be resected and the capsule wall.

The excised pieces of prostatic tissue are then pushed into the bladder either by the irrigation fluid exiting the distal end of inner sheath 2, or by manually pushing the tissue with delivery end 13 of outer sheath 4. It is preferable to position the excised pieces of prostatic tissue in the bladder so that morcellation removal of this tissue can be performed in the relatively large and safe space of the bladder, to minimize the risk of damaging adjacent tissue.

Although incising the targeted prostatic tissue with laser energy provides superior results compared to TURP (less bleeding and catheterization time), an electrosurgical device 110 can be used with resectoscope 1 as the incisional device to incise the targeted prostate tissue, as illustrated in FIG. 1C, instead of using optical fiber 20 and laser system 22. The electrosurgical device 110 includes two leads 112 connected together at their distal ends with an electrosurgical cutting loop 114. The leads 112 extend through the input port 21, along the inside length of the inner sheath 2, and out the delivery end 13 of outer sheath 4 (the same path as optical fiber 20 in the embodiment of FIGS. 1A/B). The proximate ends of leads 112 are connected to a power source 116, for passing electrical current through leads 112. Handle assembly 118, through which leads 112 pass, slides along telescope 14. By grasping handle assembly 118 and handle 120 (attached to proximate end 3 of inner sheath 2), the leads 112 are fed through port 21 to retract and project loop 114 in and out relative to delivery end 13 of outer sheath 4. When the power source 116 is activated, electrical current passes through leads 112 and loop 114, which then becomes an efficient cutting tool for incising the targeted prostatic tissue. The electrically energized loop 114 is used to incise off large pieces of the targeted prostatic tissue.

Figure 2A:
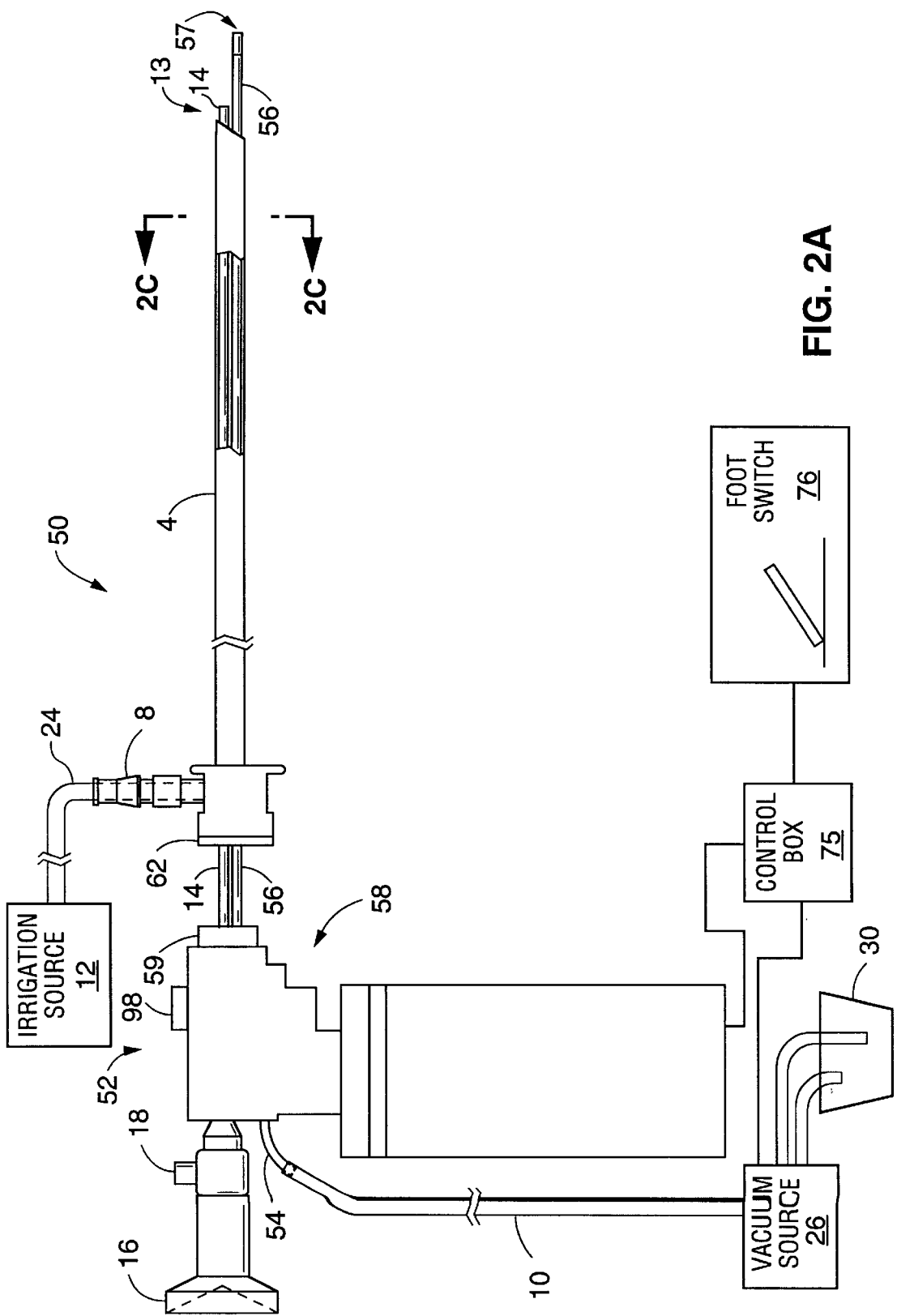
FIG. 2A is a side view of the transurethral morcellation scope of the present invention.
Figure 2B:
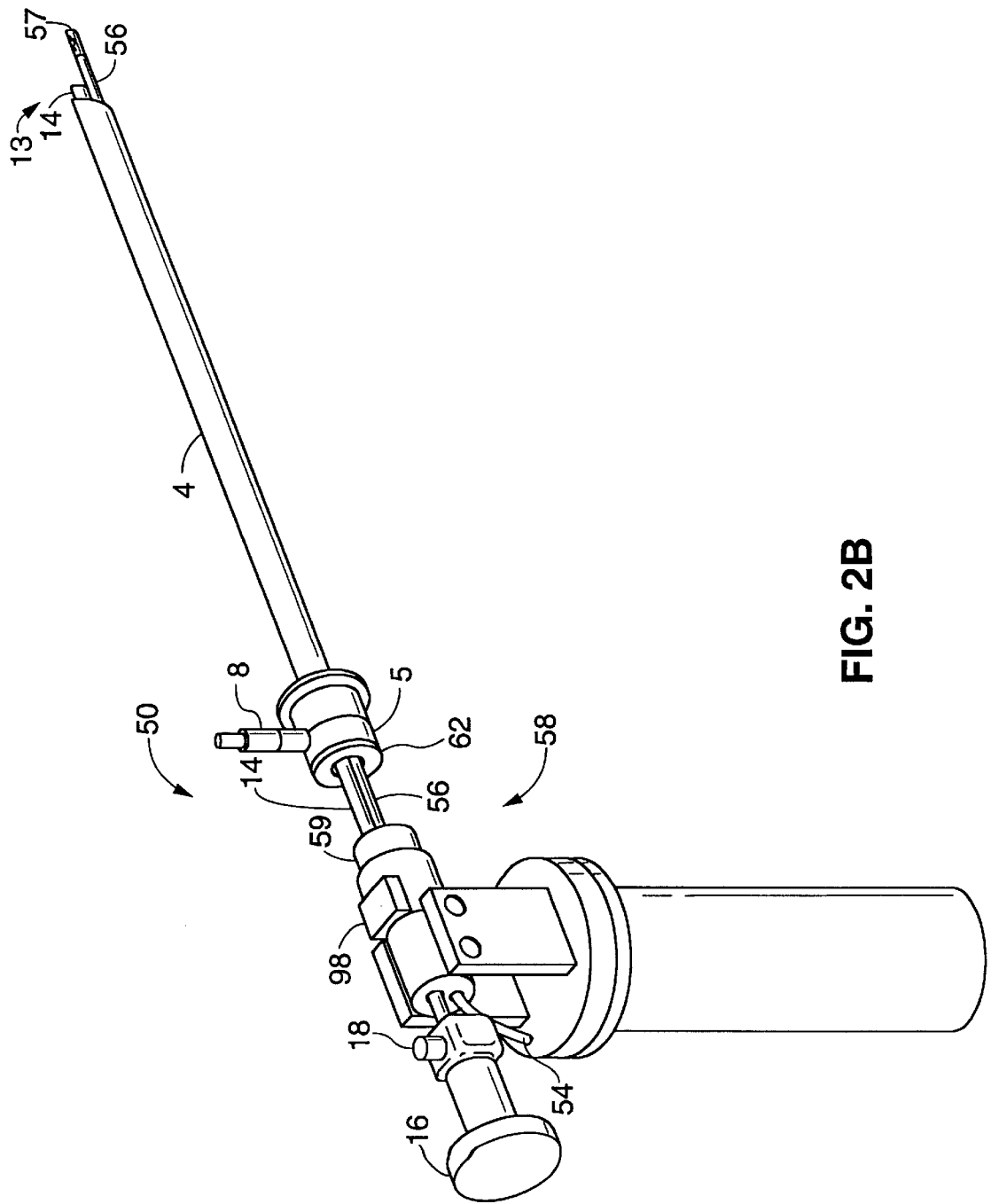
FIG. 2B is a perspective view of the transurethral morcellation scope of the present invention.
Figure 2C:
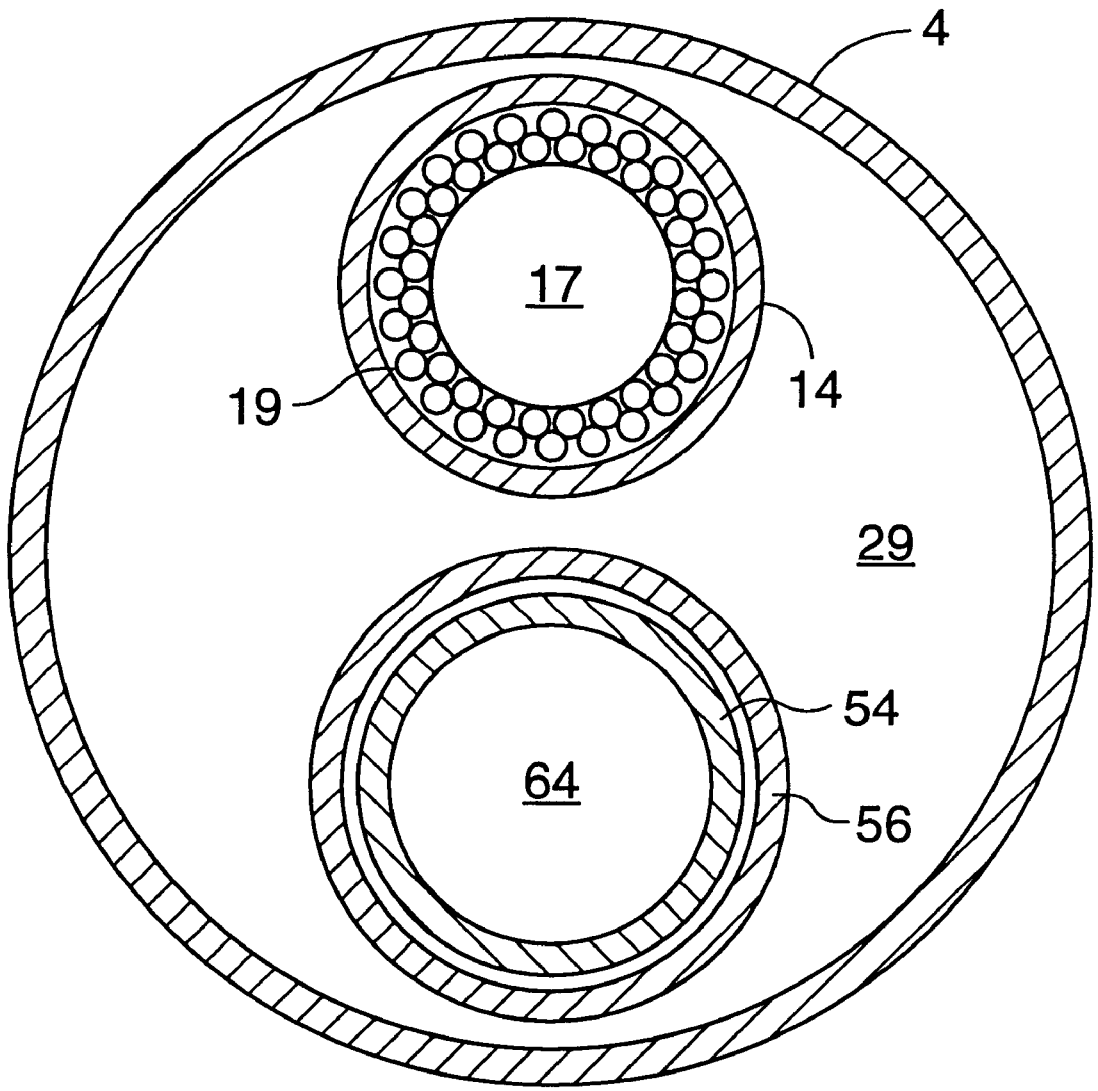
FIG. 2C is a cross-sectional end view of the transurethral morcellation scope of the present invention.

After all the targeted prostatic tissue has been incised off and pushed into the bladder, the resectoscope 1 is replaced with, or reconfigured into, the morcellation scope 50 illustrated in FIGS. 2A–2C.

Morcellation scope 50 includes the same outer sheath 4, port 8, line 24, irrigation source 12, vacuum source 26, line 10 and telescope 14 as the resectoscope 1. However, line 24 from irrigation source 24 is connected to port 8, and thus aspiration channel 6 of resectoscope 1 becomes irrigation channel 29 inside outer sheath 4.

Figure 3A:
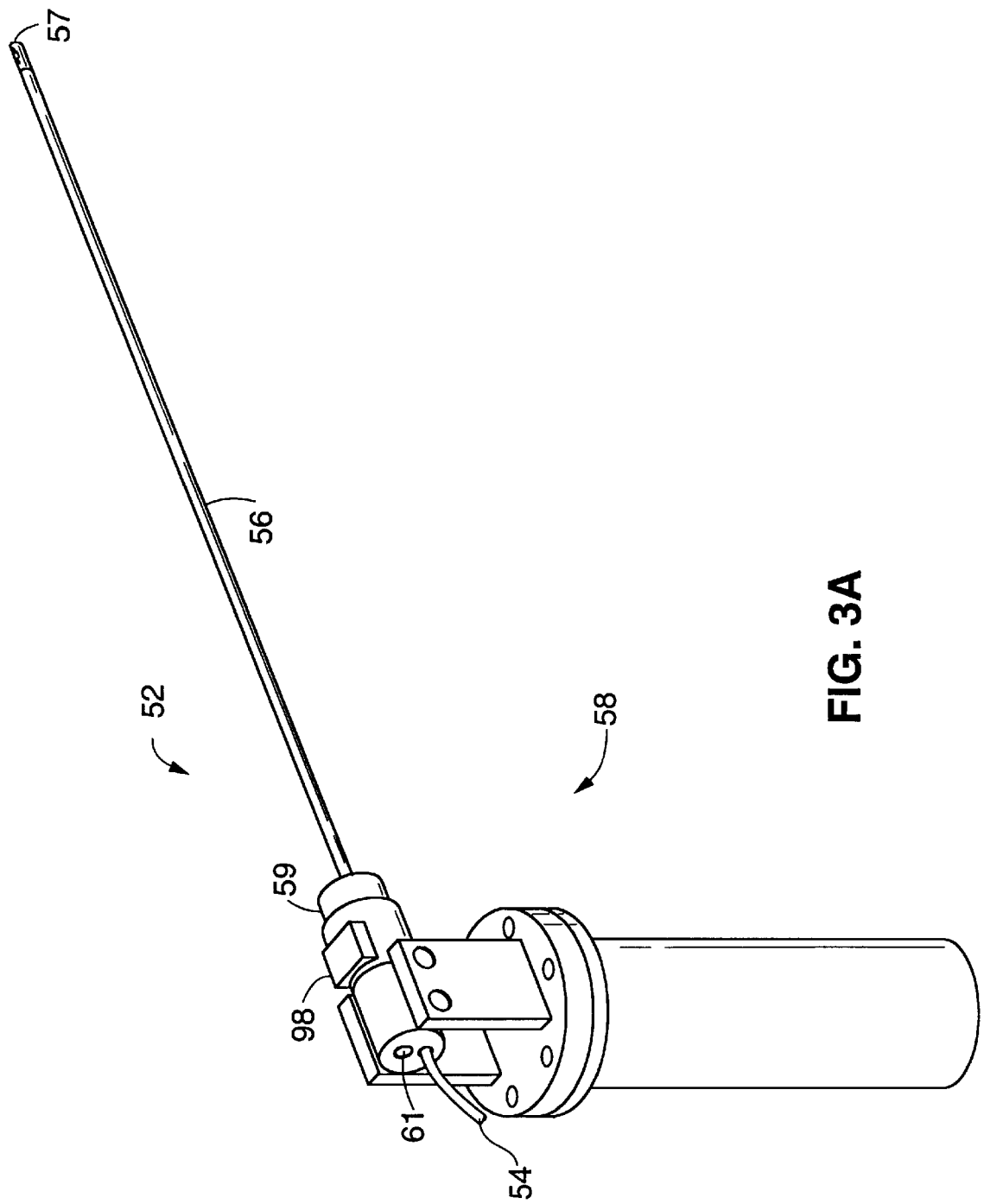
FIG. 3A is a perspective view of the morcellation probe of the present invention.
Figure 3B:
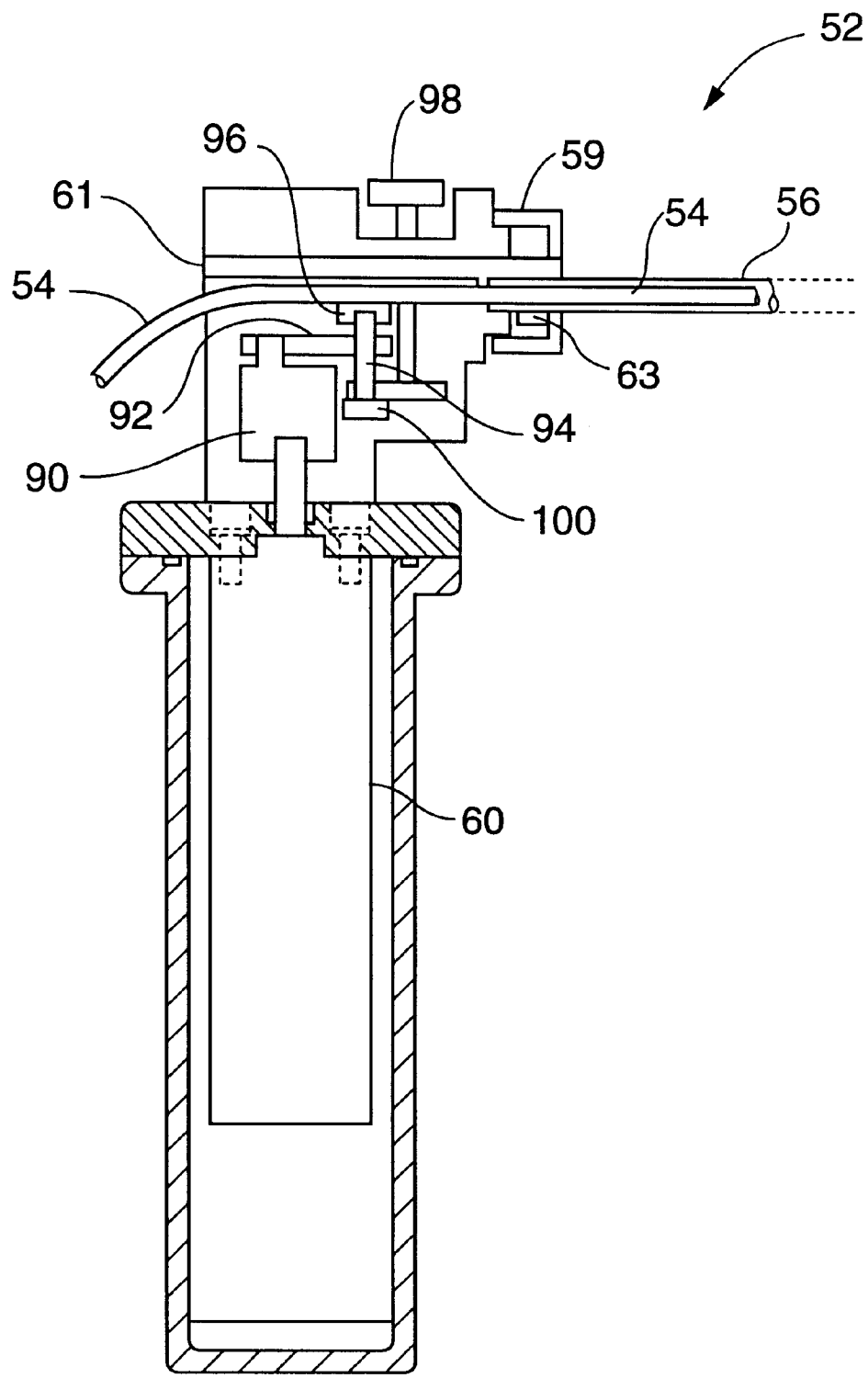
FIG. 3B is a cross-sectional view of the morcellation probe of the present invention.

Morcellation scope 50 also includes a morcellation probe 52, as illustrated in FIGS. 3A–3B, having a motor assembly 58, and an inner tube 54 slidably disposed inside an outer tube 56. Tubes 54/56 extend inside and along the length of outer sheath 4. The proximate end of outer tube 56 mounts to the motor assembly 58 via a threaded locking nut 59 that engages a bushing 63 attached to the outer tube 56.

The inner tube 54 extends through motor assembly 58, with the proximate end thereof protruding out the back side of motor assembly 58 with a downward bend to allow clearance for the eyepiece 16. Aspiration line 24 from vacuum source 26 connects to the proximate end of the inner tube 54. Inner tube 54 defines an aspiration channel 64 therein. The distal end 55 of inner tube 54, and the distal end 57 of outer tube 56, extend out the delivery end 13 of the outer sheath 4.

The telescope 14 inserts through a telescope guide channel 61 in the motor assembly 58, and extends through outer sheath 4 parallel to inner/outer tubes 54/56. A seal 62 attaches to the proximate end 5 of outer sheath 4 and forms a seal around telescope 14 and outer tube 56 to prevent irrigation fluid from leaking therefrom. Preferably, seal 62 fixably clamps telescope 14 to outer sheath 4, while allowing outer tube 56 to slide freely relative to outer sheath 4. The motor assembly 58 is then freely slidable along telescope 14 between the illumination port 18 and proximate end 5 of outer sheath 4. Sliding the motor assembly 58 along the telescope 14 extends and retracts the distal end 57 of outer tube 56 relative to the delivery end 13 of outer sheath 4.

In the preferred embodiment of morcellation probe 52, the motor assembly 58 includes a motor 60 that rotates a cam 90, which in turn drives a cam lever 92 in a reciprocating motion, as best illustrated in FIG. 3B. The cam lever 92 is engaged with a pin 94, which engages with a bushing 96 that is attached to the inner tube 54. Rotation of the cam 90 by motor 60 drives the inner tube 54 in a reciprocating motion within outer tube 56. Pin 94 can be disengaged from bushing 96 by movement of push button 98, which pushes down on end-flange 100 of pin 94. Once pin 94 is disengaged from bushing 96, inner tube 54 can be removed from the motor assembly 58 and the outer tube 56 (i.e. for replacement, sterilization, etc).

Figure 4A:
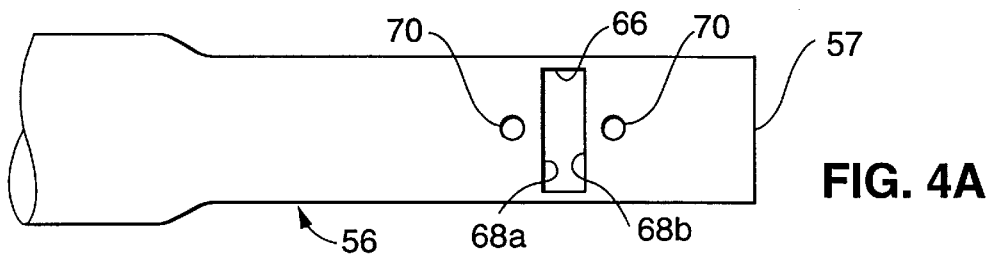
FIG. 4A is a top view of the distal end of the outer tube for the morcellation probe.
Figure 4B:
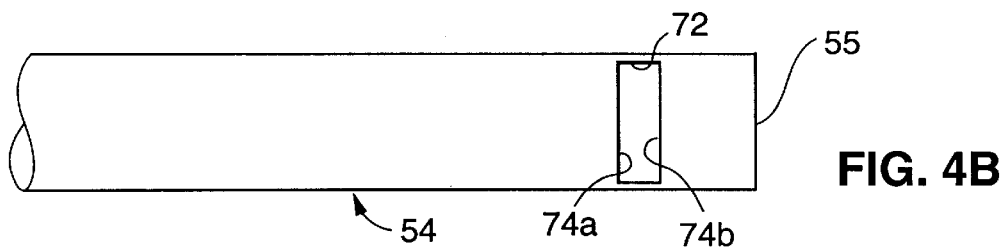
FIG. 4B is a top view of the distal end of the inner tube for the morcellation probe.

The distal ends 55/57 of inner/outer tube 54/56 are illustrated in FIGS. 4A and 4B. An aperture 66 is formed adjacent the distal end 57 of outer tube 56, with cutting edges 68a and 68b. Ports 70 are formed adjacent to the cutting edges 68a/b. An aperture 72 is formed adjacent the distal end 55 of inner tube 54, with cutting edges 74a and 74b.

Figure 5A:
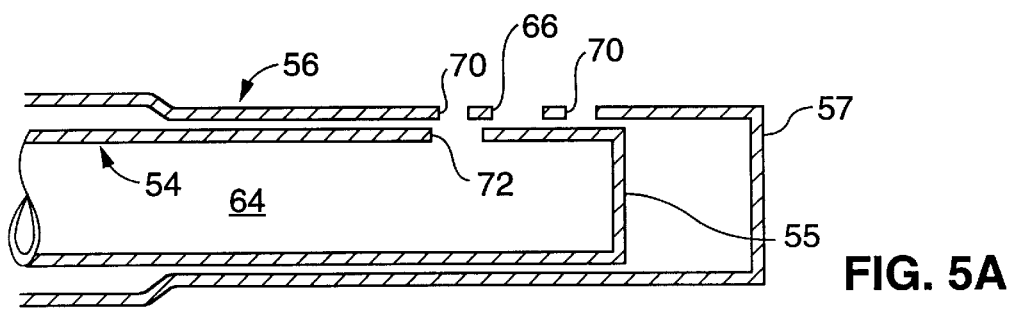
FIGS. 5A–5C are side cross-sectional views of the morcellation probe distal end, illustrating the different positions of the reciprocating inner tube.
Figure 5B:
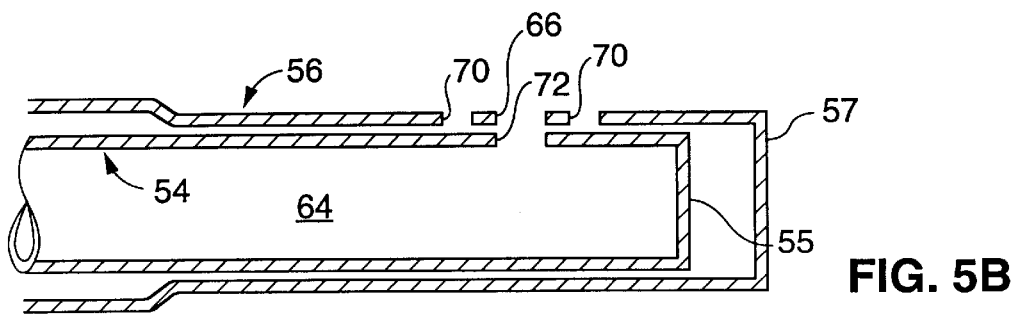
Figure 5C:
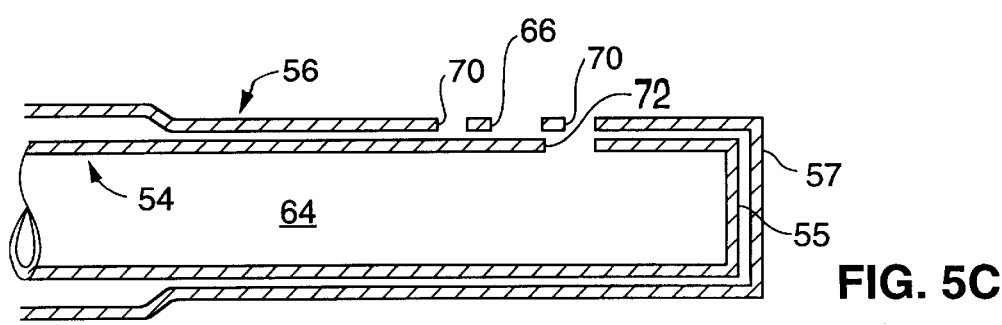

During the reciprocating motion of the inner tube 54, the inner tube 54 travels between three positions: a retracted position (FIG. 5A), a medial position (FIG. 5B), and an extended position (FIG. 5C). In the medial position, the apertures 66 and 72 fully overlap each other, thus providing direct access to the aspiration channel 64. In the retracted and extended positions, the inner tube 54 seals aperture 66 and one of the ports 70, while providing access to aspiration channel 64 through the other of the ports 70.

Ideally, the diameter of the outer tube 56 is tapered down in diameter near distal end 57, as shown in FIG. 4A. Tapering down outer tube 56 isolates and reduces the running friction between the outer tube 56 and inner tube 54 and achieves a tight, small diametrical tolerance between the inner and outer tube 54/56 adjacent the tube ends 55/57, which enhances the cutting action of the reciprocating motion between these tubes. By limiting the precise, tight clearance between tubes 54/56 to the length of the tapered section of outer tube 56, fabrication costs are reduced, the device is less sensitive to slightly bent or deflected tubes 54/56, and binding of inner tube 54 inside outer tube 56 is prevented.

A control box 75, connected to a footswitch 76, operates the vacuum source 26 and motor 60. Slightly depressing the footswitch 76 activates the vacuum source 24 to create a low level aspiration action (suction) through apertures 66/72 and ports 70. Depressing the footswitch further increases the vacuum from source 24, and thereby increases the aspiration action through apertures 66/72 and ports 70. Further depression of the footswitch causes the motor 60 to activate and drive the inner tube 54 in the reciprocation motion at a predetermined rate relative to the outer tube 56. Gradually increasing the depression of footswitch 76 results in a gradual increase in the vacuum from source 24 and/or the speed of reciprocation of the inner tube 54 by motor 60. The control box 75 can be set to provide the desired combination of suction and motor speed at various positions of the footswitch 76.

The morcellation procedure of the present inventive method is carried out by inserting the morcellation scope 50 through the urethra until the delivery end 13 is positioned in the bladder. The irrigation source 12 is then activated. The surgeon, viewing through the eyepiece 16, locates a piece of prostatic tissue that had previously been deposited in the bladder. By activating the vacuum source 26 at a low vacuum setting with footswitch 76 and positioning the distal end 57 of outer tube 56 adjacent the targeted piece of prostate, the low level aspiration action of the probe draws the tissue to, and attaches the tissue against, the apertures 66/72 and ports 70. The surgeon then re-positions the distal end 57 of outer probe 56, with the target tissue attached thereto, toward the center of the bladder, where it is safe to operate the morcellation probe without damaging surrounding tissue.

Figure 6A:
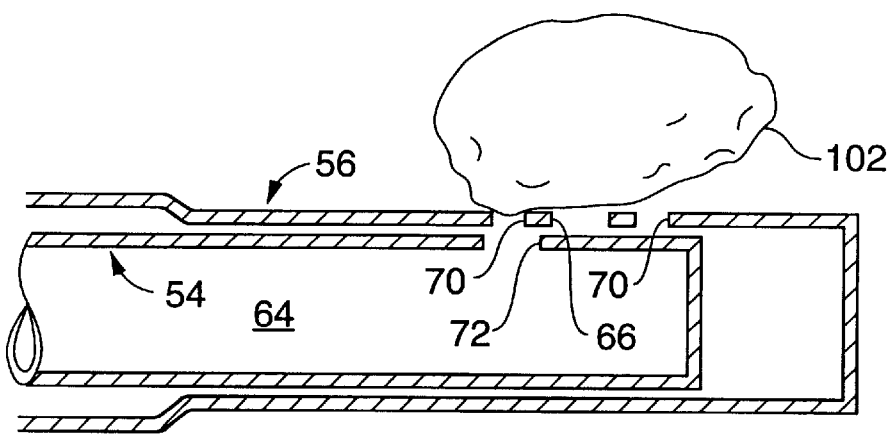
FIGS. 6A–6C are side cross-sectional views of the morcellation probe distal end, illustrating the cutting action of the inner and outer tubes.
Figure 6B:
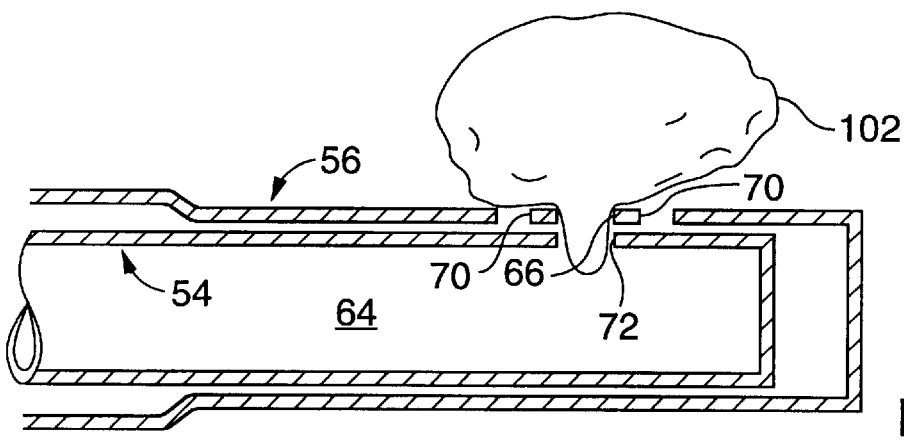
Figure 6C:
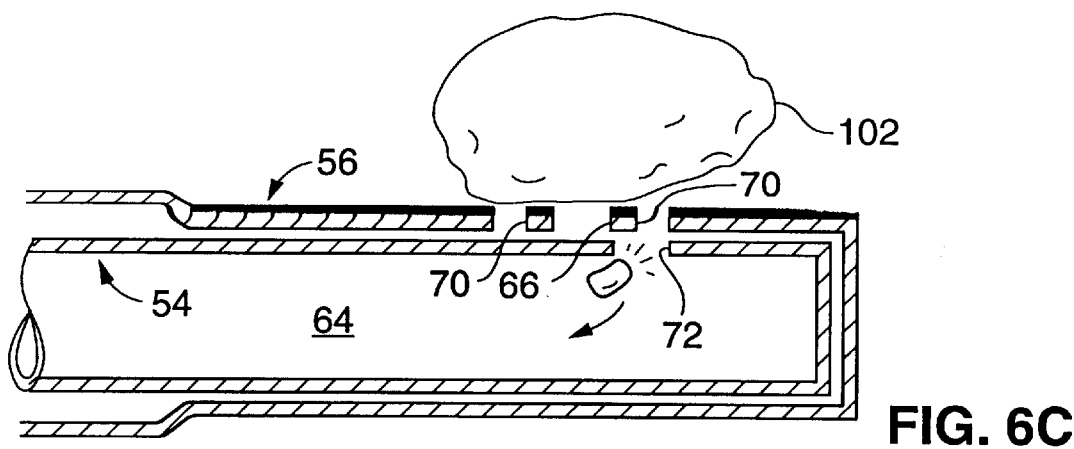

Once the tissue and outer probe tube distal end 57 are positioned away from the bladder walls, the surgeon depresses the footswitch 76 further until motor 60 is activated at the desired speed. The reciprocating action of inner tube 54 together with the aspiration from the vacuum source 26 efficiently morcellates the targeted prostatic tissue (cuts the tissue into very small pieces), and aspirates the targeted tissue from the patient. As illustrated in FIGS. 6A–6C, when the apertures 66/72 become misaligned (for example during movement from the medial position to the extended position), the small portion of tissue 102 drawn into the apertures 66/72 is cut by the approaching cutting edges 74a and 68b, and aspirated out of the patient via the aspiration channel 64 and aspiration line 24. The ports 70 function to manipulate the targeted tissue position by maintaining continuous aspiration adjacent aperture 66. The continuous aspiration prevents the targeted tissue mass 102 from disengaging from aperture 66 so that upon reverse reciprocal motion of inner tube 54, another portion of the tissue mass 102 will be drawn through apertures 68/72 for cutting/aspiration using cutting edges 74b and 68a. The surgeon need only maintain the position of the distal end 57 of tube 56 away from the bladder walls and allow the morcellation probe 52 to efficiently and quickly morcellate the target tissue 102 bit by bit until fully morcellated and aspirated out of the patient. Once the tissue is fully aspirated out of the patient, the footswitch is released to cease the reciprocation motion of inner tube 54 and to lower the aspiration to a safe level, so that the next piece of excised prostatic tissue can be retrieved and morcellated.

During each reciprocation cycle of the inner tube 54, two cutting actions occur. When the inner tube 4 reaches the retracted position of FIG. 5A or the extended position of FIG. 5C, aperture 66 is momentarily sealed. Continuous aspiration provided through ports 70 positioned on either side of aperture 66 helps maintain a position of the targeted tissue mass 102 that is disposed over aperture 66. This positioning of the target tissue maximizes the morcellation efficiency, and maintains the tissue attachment to outer tube 56, which prevents the surgeon from having to cease the motor operation to retrieve dislodged pieces of target tissue.

Also during each cycle, cutting edges 74a and 74b alternately pass and seal ports 70 at different times. This cutting and sealing action at ports 70 serves an important self cleaning function, so that any tissue or debris that may clog the ports 70 is cut and aspirated, or released. If one of ports 70 becomes clogged, then continuous aspiration may be lost, which could result in disengagement of the target tissue 102 from the probe 52, thus reducing morcellation efficiency.

Ideally, outer sheath 4 is inserted into the urethra only once during the prostate resection procedure. Therefore, resectoscope 1 can be reconfigured to morcellation scope 50 without removing outer sheath 4 from the patient. After the targeted prostatic tissue is incised and pushed into the bladder with the resectoscope 1, the inner sheath 2 (containing the telescope 14 and either the optical fiber 20 or electrosurgical leads 112 and loop 114) is detached from, and slid rearwardly out of, outer sheath 4. The telescope 14 is removed from inner sheath 2 and inserted through telescope guide channel 61 in the motor assembly 58. The aspiration line is detached from port 8 and attached to the proximate end of inner tube 54. The irrigation line is detached from port 25 and attached to port 8. Seal 62 is then placed over the telescope 14 and outer tube 56. Telescope 14 and outer tube 56 are inserted into the outer sheath 4, whereby seal 62 is affixed to the proximate end 5 of outer sheath 4 for sealing the telescope 14 and outer tube 56 in place.

Figure 7A:
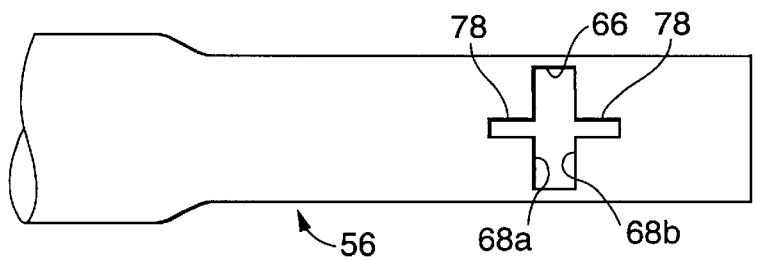
FIGS. 7A/B are top views of an alternate embodiment of the morcellation probe of the present invention.
Figure 7B:
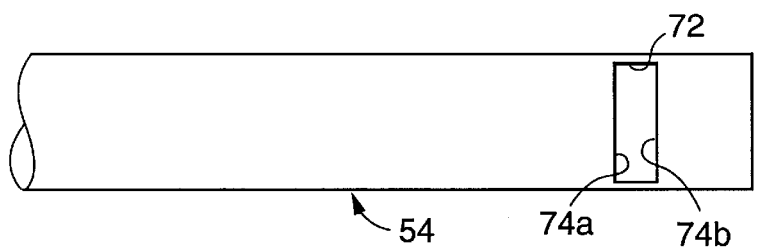
Figure 8A:
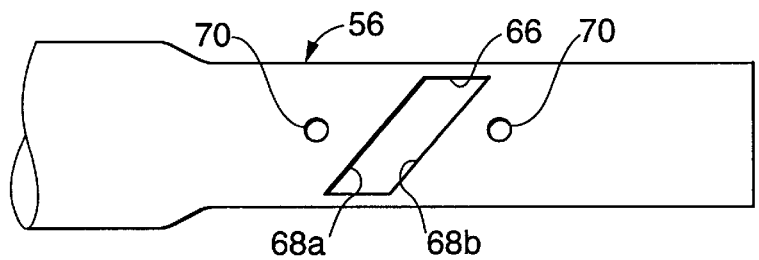
FIGS. 8A/B are top views of a second alternate embodiment of the morcellation probe of the present invention.
Figure 8B:
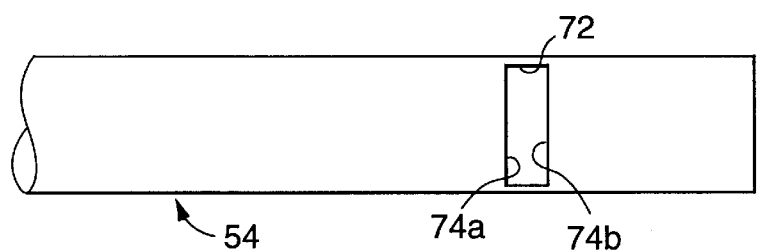
Figure 9A:
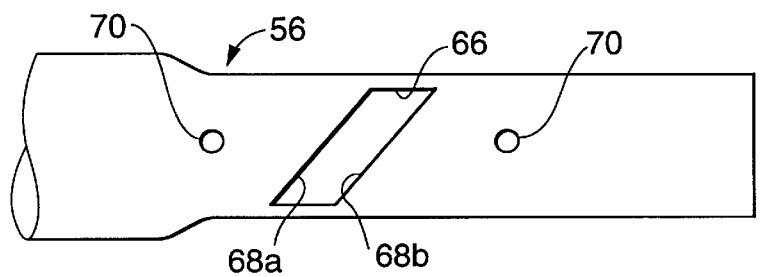
FIGS. 9A/B are top views of a third alternate embodiment of the morcellation probe of the present invention.
Figure 9B:
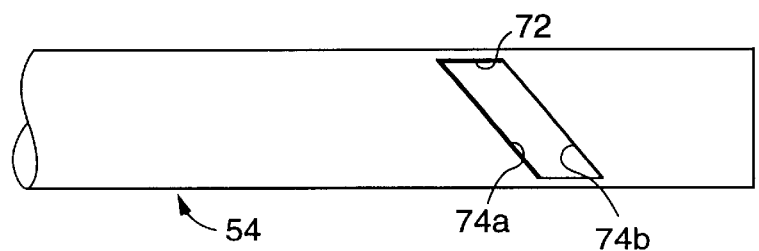
Figure 10A:
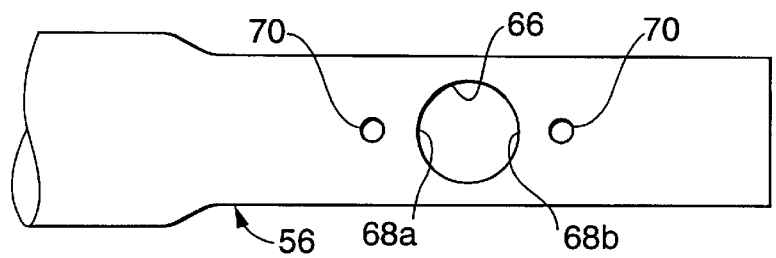
FIGS. 10A/B are top views of a fourth alternate embodiment of the morcellation probe of the present invention.

The aspiration apertures 66 and 72, and ports 70, can have various shapes and configurations. For maximum morcellation efficiency, these various shapes and configurations should maintain the continuous aspiration adjacent aperture 66 throughout the reciprocating motion of the inner tube 54, while incorporating the self-cleaning feature of closing off any apertures or ports in the outer tube 56 at least once during the reciprocating cycle. For example, FIGS. 7A and 7B illustrate slots 78 formed continuously with aperture 66, for providing continuous aspiration. Alternately, the cutting edges 68a/b of aperture 66 can be angled relative to cutting edges 74a/b as shown in FIGS. 8A and 8B, which decreases the peak cutting power required to cut tissue by cutting tissue in a continuous scissor-like action, instead of the relatively instantaneous cutting action from parallel cutting edges passing each other. For even more cutting power, the cutting edges 74a/b can be angled in the opposite direction as the angled cutting edges 68a/b of aperture 66 as shown in FIGS. 9A and 9B. Apertures 66/72 can instead be circular shaped, as shown in FIGS. 10A/B.

Figure 11A:
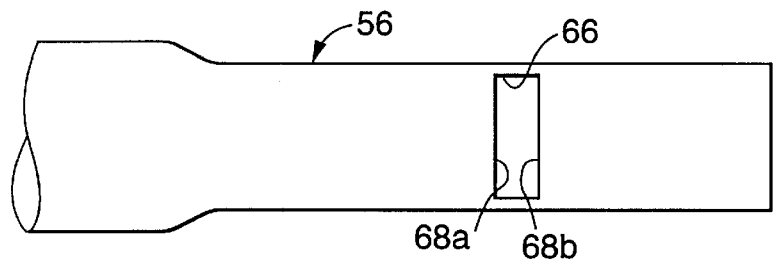
FIGS. 11A/B are top views of a fifth alternate embodiment of the morcellation probe of the present invention.
Figure 11B:
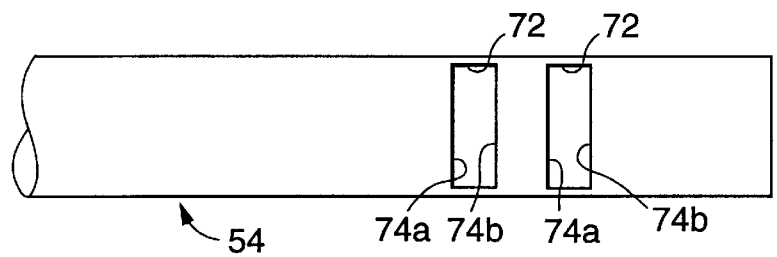
Figure 12A:
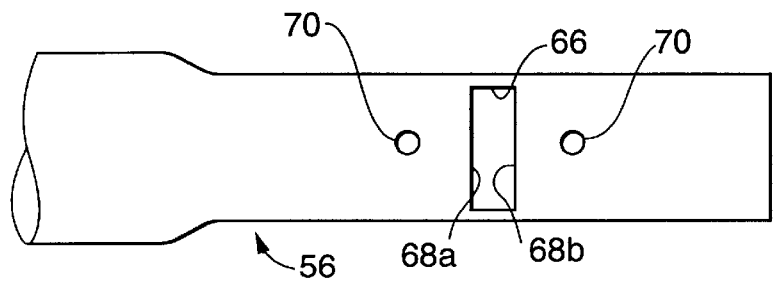
FIGS. 12A/B are top views of a sixth alternate embodiment of the morcellation probe of the present invention.
Figure 12B:
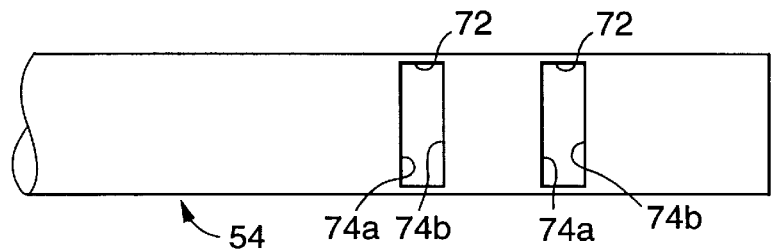

A second aperture 66 or 72 can be formed on outer/inner tubes 56/54, as shown in FIGS. 11A/B, 12A/B, 14A/B and 15A/B, to increase the cutting action per cycle. If multiple apertures formed on the same inner or outer tube 54/56 are close enough together, and the travel of inner tube 54 is limited to maintain continuous aspiration, ports 70 can be eliminated (i.e. FIGS. 11A/B).

Figure 13A:
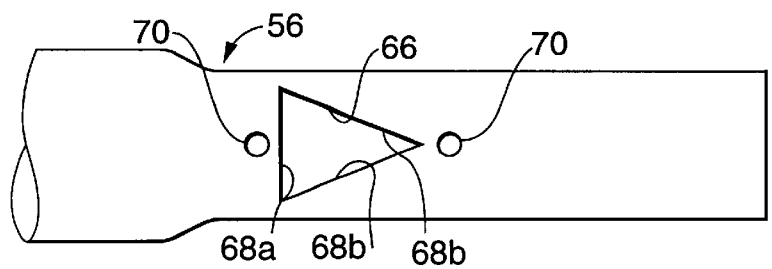
FIGS. 13A/B are top views of a seventh alternate embodiment of the morcellation probe of the present invention.
Figure 13B:
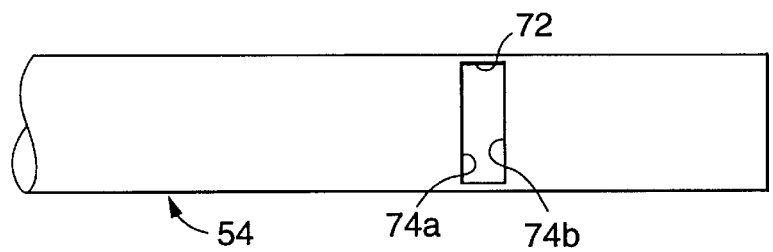
Figure 14A:
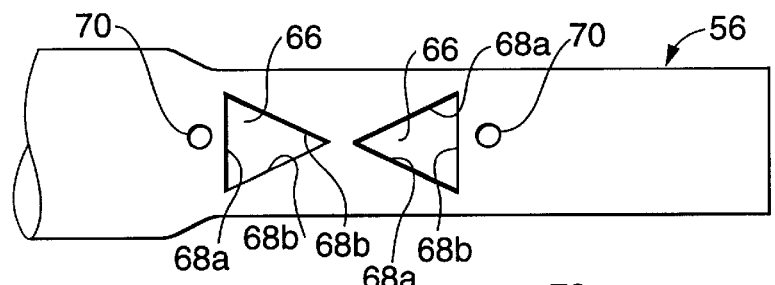
FIGS. 14A/B are top views of a eighth alternate embodiment of the morcellation probe of the present invention.
Figure 14B:
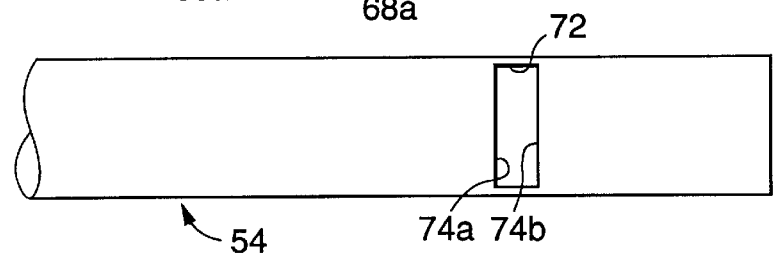
Figure 17A:
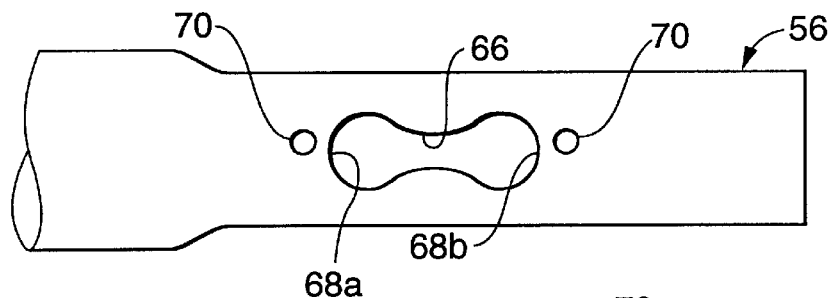
FIGS. 17A/B are top views of a eleventh alternate embodiment of the morcellation probe of the present invention.
Figure 17B:
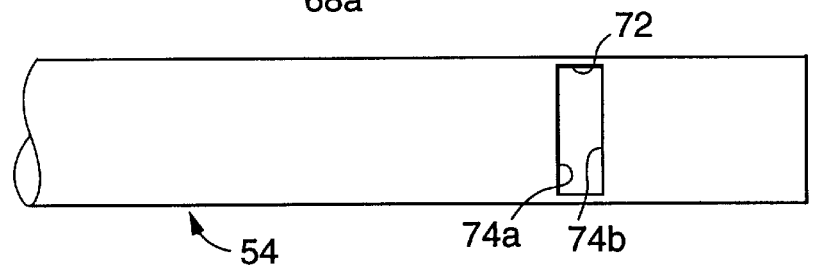

The shape and numbers of apertures 66 and 72, and ports 70, formed on outer/inner tubes 56/54 can be varied to achieve the desired cutting action, as illustrated in FIGS. 13A/B, 14A/B, 15A/B, 16A/B and 17A/B. The cutting edges can be non-linear (FIGS. 10A/B, 13A, 14A, and 15A/B) or irregularly shaped (FIG. 17A) to provide varying cutting angles between the cutting edges 68a and 74b, and/or between 68b and 74a, during one or both cutting actions per reciprocation cycle of inner tube 54.

Figure 18A:
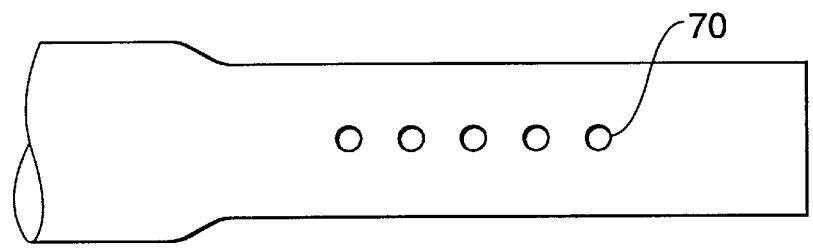
FIGS. 18A/B are top views of a twelfth alternate embodiment of the morcellation probe of the present invention.
Figure 18B:
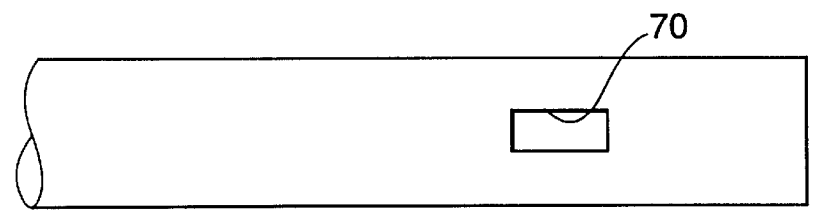

If additional fluid is needed to aspirate the morcellated tissue without clogging aspiration channel 64, additional ports 70 can be added to inner/outer tubes 54/56, as illustrated in FIGS. 18A/B. These additional ports 70 should be located away from aperture 66, for example on the opposing underneath side of inner/outer tubes 54/56, such that they do not manipulate the targeted tissue. The additional ports 70 will supply additional fluid to the aspiration channel 64 when in a fluid environment to prevent blockage thereof without manipulating the targeted tissue being morcellated by apertures 66/72. These additional ports 70 should be sealed at least once per reciprocation cycle to prevent clogging thereof.

Figure 10B:
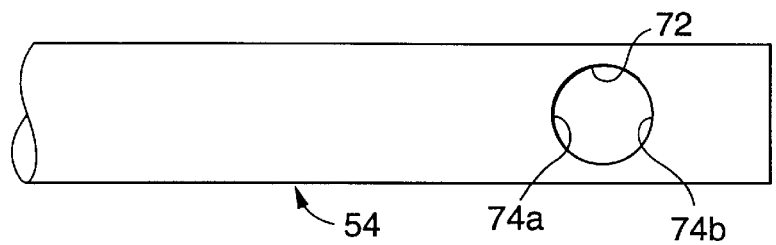
Figure 15A:
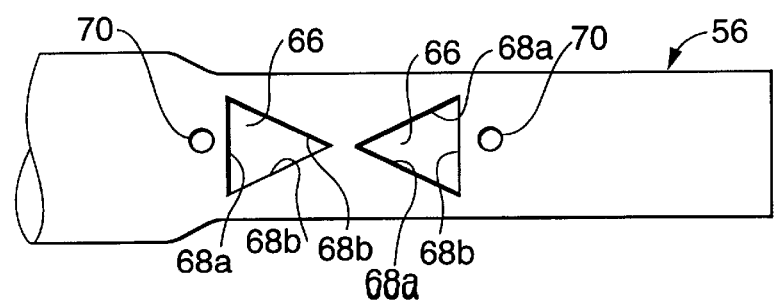
FIGS. 15A/B are top views of a ninth alternate embodiment of the morcellation probe of the present invention.
Figure 15B:
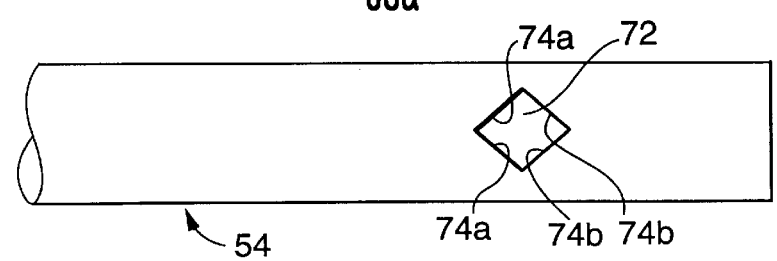
Figure 16A:
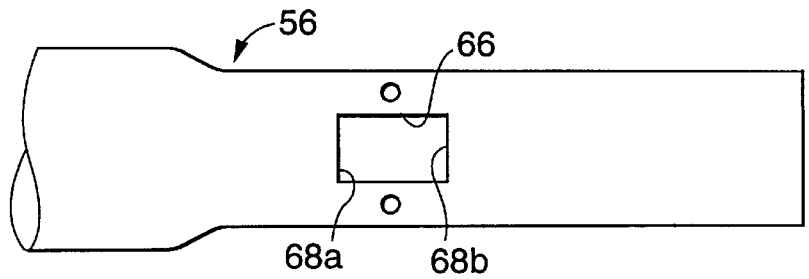
FIGS. 16A/B are top views of a tenth alternate embodiment of the morcellation probe of the present invention.
Figure 16B:
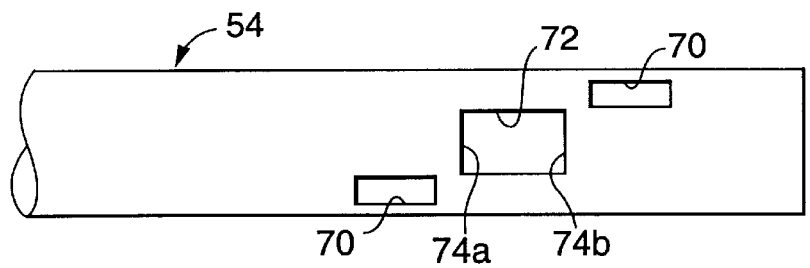
Figure 19A:
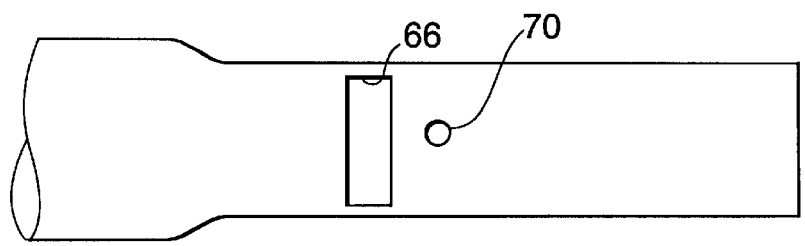
FIGS. 19A/B are top views of a thirteenth alternate embodiment of the morcellation probe of the present invention.
Figure 19B:
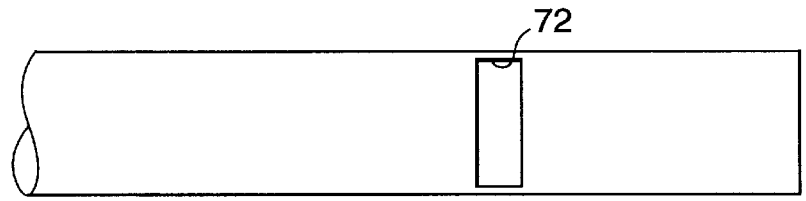

It should be noted that it is well within scope of the present invention to combine different variations of the patterns of apertures/ports illustrated herein to achieve the desired cutting action of the morcellation probe 52. For example, any or all apertures and ports shown on outer tube 56 can instead be formed on inner tube 54, and vice versa (i.e. one or both ports 70 in FIGS. 4A/B etc. can be formed on inner tube 54 instead of outer tube 56, or apertures 66 of FIG. 15A can be formed on inner tube 54 and aperture 72 of FIG. 15B can be formed on outer tube 56, etc.). Further, part or all of the aperture/port pattern of inner tube 54 in one figure can be used with part or all of the aperture/port pattern of outer tube 56 in other figure (i.e. inner tube 54 of FIG. 10B can be used with outer tube 56 of FIG. 11A). Moreover, additional sets of aperture and port patterns can be added to those illustrated in the figures, either longitudinally along, or rotatably around, tubes 54/56. For example, the apertures and ports of FIGS. 7A/B could formed on a top side of inner/outer tubes 54/56, and the apertures and ports of FIGS. 8A/B could be formed on an opposing bottom side of the inner/outer tubes 54\56. Lastly, for some applications, it may be possible to have a single port 70 as shown in FIGS. 19A\B and either limit travel of the inner tube 54 to not seal aperture 66 when the inner tube is in the retracted position, or have intermittent loss of continuous aspiration once per cycle while still maintaining proper tissue position (i.e. through very high repetition rates in conjunction with the single port 70).

Figure 20A:
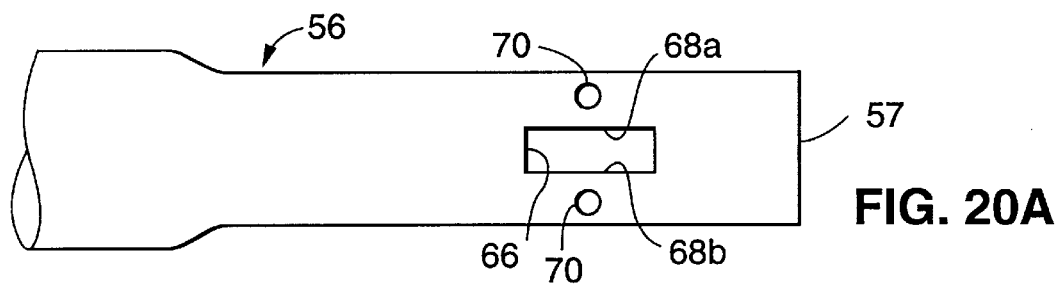
FIGS. 20A/B are top views of a rotating morcellation probe embodiment of the present invention.
Figure 20B:
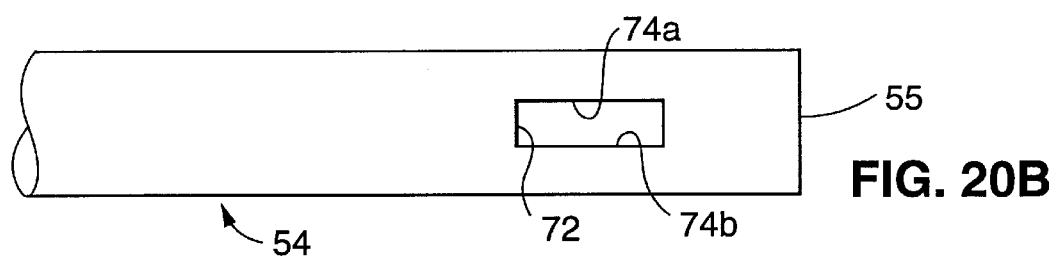

While the preferred embodiment of morcellation probe 52 has been described above as longitudinally reciprocating the inner tube 54 relative to the outer tube 56, the scope of the present invention also includes using a rotating morcellator, where inner tube 54 spins about its longitudinal axis relative to outer tube 56. For a rotating morcellator, the aperture/port patterns illustrated in FIGS. 4A/B and 7A/B–19A/B are formed around tubes 54/56 instead of along the longitudinal length of tubes 54/56 (i.e. the patterns are rotated 90°). For example, FIGS. 20A/B illustrate the 90° reorientation of the aperture/ports patterns shown in FIGS. 4A/B. Therefore, as inner tube 54 rotates relative to outer tube 56, tissue drawn into the apertures 66/72 is cut by the approaching cutting edges 68a and 74b, and cutting edges 68b and 74a. Motor 60 rotates inner tube 54 about its longitudinal axis either continuously in one direction, or in an oscillating fashion. To maintain constant aspiration where the inner tube 54 rotates continuously in one direction, the aperture/port patterns can be formed all the way around the inner/outer tubes 54/56. If the inner tube 54 rotationally oscillates, then constant aspiration is achieved by rotating between two rotational positions in the same manner as longitudinally reciprocating between the two extended/retracted positions as described above.

Figure 21A:
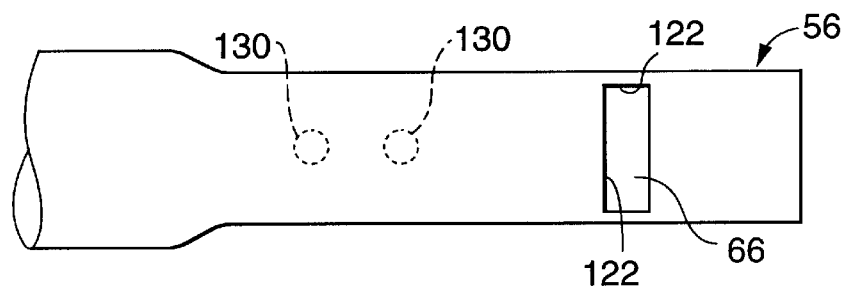
FIGS. 21A/B are top views of an auger type morcellation probe embodiment of the present invention.
Figure 21B:
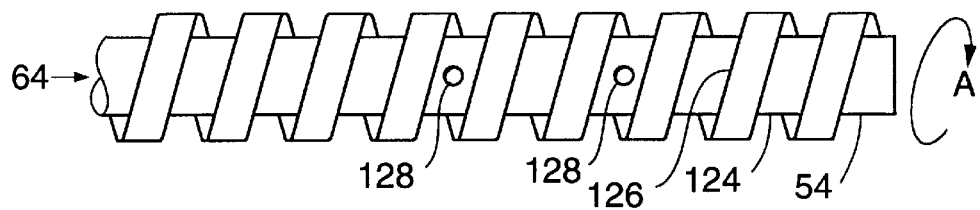

FIGS. 21A/B illustrate another embodiment of the present invention: an auger type morcellation probe 52. Outer tube 56 has an aperture 66 with cutting edges 122. A spiral shaped groove 124 is formed on the outer surface of inner tube 54, either along its entire length or preferably on just a portion near its distal end. The spiral shaped groove 124 forms a continuous cutting edge 126 for cutting tissue against cutting edges 122 of aperture 66. One or more aspiration ports 128 are formed in groove 124 (preferably at the bottom of groove 124) and are continuous with aspiration channel 64. Fluid ports 130 can be formed in outer tube 56, located away from aperture 66 (i.e. on the opposing underneath side of outer tube 56) for supplying additional fluid to aspiration ports 128 without manipulating the targeted tissue outside aperture 66. When the inner tube 54 is rotated about its longitudinal axis relative to outer tube 56 in the direction of arrow A, tissue drawn into aperture 66 is cut by cutting edge 126 passing beyond cutting edges 122. The cut tissue is drawn along groove 124, through aspiration ports 128, and out through aspiration channel 64. Continuous aspiration through aperture 66 is preserved because at least some portion of groove 124 is exposed to aperture 66 at all times. Aperture 66 can have any of the aperture/ports shapes illustrated in FIGS. 7A/B–20A/B. Alternately, inner tube can have no ports 128 (and even be a solid tube with no aspiration channel 64 therein). In that case, the vacuum source is attached to the motor assembly 58 or outer tube 56 to provide a vacuum between inner tube 54 and outer tube 56, whereby the cut tissue is aspirated by being drawn along groove 124, between inner and outer tubes 54/56, and out to the vacuum source 26.

It is to be understood that the present invention is not limited to the embodiments described above and illustrated herein, but encompasses any and all variations falling within the scope of the appended claims. For example, the surgeon may wish to morcellate some of the excised prostatic tissue while still positioned in the urethra, without pushing the excised prostatic tissue into the bladder. Further, it is conceivable to add the morcellation probe 52 to the resectoscope 1 for either simultaneous or alternate prostatic tissue incision and morcellation, without reconfiguring between scopes 1 and 52 between these steps.

What is claimed is:

1. A morcellation device for morcellating and removing targeted body tissue from within a patient, comprising:

an elongated outer probe tube defining a first interior channel therein and having a first aperture formed adjacent to a closed distal end of said outer probe tube;

an elongated inner probe tube defining an aspiration channel therein and having a longitudinal axis and a second aperture formed adjacent to a distal end of said inner probe tube, said inner probe tube being slidably disposed inside said first interior channel, a proximate end of said inner probe tube being connectable to a vacuum source, said inner probe tube movable relative to said outer probe tube between a first position where said first and second apertures at least partially overlap each other, and a second position where said first and second apertures do not overlap each other;

a tissue manipulation port formed in one of said outer probe tube adjacent said first aperture and said inner probe tube adjacent said second aperture, such that said tissue manipulation port at least partially overlaps one of said first and second apertures when said inner probe tube is in said second position; and said first aperture has a first cutting edge and said second aperture has a second cutting edge, said first and second cutting edges passing each other when said inner probe tube moves from said first position to said second position;

wherein during operation, aspiration caused by a vacuum in said aspiration channel from the vacuum source manipulates the targeted tissue to said first aperture and draws a portion of the targeted tissue into said first and second apertures when said inner probe tube is in said first position, and the portion of targeted tissue is cut by said first and second cutting edges passing each other when said inner probe tube moves from said first position to said second position, the cut portion of targeted tissue being drawn into and through said aspiration channel, the tissue manipulation port providing suction from the aspiration channel to hold the target tissue in position while said inner probe tube is in said second position.

2. The morcellation device as recited in claim 1, wherein when said outer probe tube is in said first position, said tissue manipulation port does not overlap the one of said first and second apertures.

3. The morcellation device as recited in claim 2, wherein, during said movement of said inner probe tube from said first position to said second position, the overlapping of said tissue manipulation port with the one of said first and second apertures begins before said first and second apertures cease overlapping each other, to provide continuous manipulation of the target tissue position as said inner probe tube moves from said first to said second positions.

4. The morcellation device as recited in claim 3, wherein said inner probe tube rotates about its longitudinal axis relative to said outer probe tube between said first and second positions.

5. The morcellation device as recited in claim 3, wherein said inner probe tube is movable relative to said outer probe tube in a reciprocating longitudinal movement between said first and second positions in a direction parallel to said longitudinal axis of said inner probe tube.

6. The morcellation device as recited in claim 3, wherein said tissue manipulation port is formed continuously with the other of said one of said first and second apertures.

7. The morcellation device as recited in claim 3, wherein said first and second cutting edges are non-parallel to each other.

8. The morcellation device as recited in claim 3, wherein at least one of said first and second cutting edges is arc shaped.

9. The morcellation device as recited in claim 3, wherein said first and second cutting edges are non-linearly shaped to provide a varying cutting action as said inner tube moves from said first position to said second position.

10. The morcellation device as recited in claim 5, further comprising:

a motor assembly having a motor, said motor assembly connected to a proximate end of said outer probe tube, said motor connected to said inner probe tube for driving said inner probe tube in said reciprocating longitudinal movement relative to said outer probe tube.

11. The morcellation device as recited in claim 10, further comprising:

a cam attached to said motor;

a pin engaged with said cam and removably engaged with said inner probe tube, wherein said motor rotates said cam which in turn drives said pin in a reciprocating movement, said pin is disengageable from said inner probe tube for removal of said inner probe tube from said morcellation device.

12. The morcellation device as recited in claim 10, wherein said motor assembly has a telescope port for inserting a telescope parallel to said inner and outer probe tubes.

13. The morcellation device as recited in claim 12, further comprising:

an irrigation fluid source that provides irrigation fluid into an irrigation line; and an outer sheath tube defining an irrigation channel in fluid communication with an irrigation port connected to said irrigation line, said outer sheath tube surrounding said telescope and said outer probe tube with an open end adjacent to said outer probe tube distal end for directing the irrigation fluid thereto.

14. The morcellation device as recited in claim 10, further comprising:

a footswitch connected to said motor and connectable to the vacuum source for controlling said motor and the vacuum source, wherein when said footswitch is slightly depressed, the vacuum source is activated to create a low level vacuum in said aspiration channel, and when said footswitch is depressed to a mid-position said motor is activated to drive said inner probe tube in said movement relative to said outer probe tube, wherein as said footswitch is gradually depressed beyond said mid-position, said motor and vacuum source are controlled to gradually increase the motor speed and aspiration channel vacuum.

15. The morcellation device as recited in claim 3, wherein said outer probe tube is tapered down in diameter adjacent said distal end of said outer probe tube.

16. The morcellation device as recited in claim 3, further comprising:

a first fluid port formed in said inner probe tube adjacent said distal end thereof;

a second fluid port formed in said outer probe tube adjacent said distal end thereof, wherein said first and second fluid ports are alternately overlapping and not overlapping each other during said movement of said inner probe tube between said first and second positions for supplying fluid into said aspiration channel when said distal end of said outer tube is positioned in a fluid environment, said first and second fluid ports positioned sufficiently away from said first and second apertures to not manipulate the position of the targeted tissue engaged therewith.

17. A morcellation device for morcellating and removing targeted body tissue from within a patient, comprising:

an elongated outer probe tube defining a first interior channel therein and having a first aperture formed adjacent to a closed distal end of said outer probe tube, said first aperture having opposing first and second cutting edges;

an elongated inner probe tube defining an aspiration channel therein and having a longitudinal axis and a second aperture formed adjacent to a distal end of said inner probe tube, said second aperture having opposing third and fourth cutting edges, said inner probe tube being slidably disposed inside said first interior channel, a proximate end of said inner probe tube being connectable to a vacuum source, said inner probe tube being movable relative to said outer probe tube between a first position, a second position, and a medial position which is between said first and second positions, said first and second apertures at least partially overlap each other when said inner probe tube is in said medial position, said first and second apertures not overlapping each other when said inner probe tube is in either of said first and second positions;

a first tissue manipulation port, formed adjacent to one of said first and third cutting edges, that overlaps with one of said first and second apertures when said inner probe tube is in said first position; and a second tissue manipulation port, formed adjacent to one of said second and fourth cutting edges, that overlaps with one of said first and second apertures when said inner probe tube is in said second position;

wherein during operation, aspiration caused by a vacuum in said aspiration channel from the vacuum source manipulates the targeted tissue to said first aperture and draws a portion of the targeted tissue into said first and second apertures when said inner probe tube is in said medial position, and the portion of targeted tissue is cut by said first and third cutting edges passing each other when inner tube moves from said medial position to said first position and by said second and fourth cutting edges passing each other when said inner tube moves from said medial position to said second position, the cut targeted tissue being drawn into and through said aspiration channel, said first and second tissue manipulation ports providing suction from the aspiration channel to hold the target tissue in position while said inner probe tube is in said first and second positions.

18. The morcellation device of claim 17, wherein:
said first tissue manipulation port does not overlap with the one of said first and second apertures when said inner probe tube is in said second position; and
said second tissue manipulation port does not overlap with the one of said first and second apertures when said inner probe tube is in said first position.

19. The morcellation device of claim 18, wherein:
during said movement of said inner probe tube from said medial position to said first position, said overlapping of said first tissue manipulation port with the one of said first and second apertures begins before said first and second apertures cease overlapping each other, and
during said movement of said inner probe tube from said medial position to said second position, said overlapping of said second tissue manipulation port with the one of said first and second apertures begins before said first and second apertures cease overlapping each other, wherein continuous manipulation of the target tissue position is provided as the inner probe tube travels from said first position to said second position.

20. The morcellation device as recited in claim 19, wherein said inner probe tube rotates about its longitudinal axis relative to said outer probe tube between said first and second positions.

21. The morcellation device as recited in claim 20, wherein said inner probe oscillates between said first and second positions thereby passing through said medial position twice during each of said oscillations.

22. The morcellation device as recited in claim 19, wherein said inner probe tube is movable relative to said outer probe tube in a reciprocating longitudinal movement between said first and second positions in a direction parallel to said longitudinal axis of said inner probe tube.

23. The morcellation device as recited in claim 19, wherein said first tissue manipulation port is formed continuously with the one of said first and third cutting edges, and said second tissue manipulation port is formed continuously with the one of said second and fourth cutting edges.

24. The morcellation device as recited in claim 19, wherein said first and third cutting edges are non-parallel to each other, and said second and fourth cutting edges are non-parallel to each other.

25. The morcellation device as recited in claim 19, wherein at least one of said first, second, third and fourth cutting edges is arc shaped.

26. The morcellation device as recited in claim 19, wherein at least one of said first, second, third and fourth cutting edges is non-linearly shaped to provide a varying cutting action as said inner tube moves away from said medial position.

27. The morcellation device as recited in claim 22, further comprising:
a motor assembly having a motor, said motor assembly connected to a proximate end of said outer probe tube, said motor connected to said inner probe tube for driving said inner probe tube in said reciprocating longitudinal movement relative to said outer probe tube.

28. The morcellation device as recited in claim 27, further comprising:
a cam attached to said motor;
a pin engaged with said cam and removably engaged with said inner probe tube, wherein said motor rotates said cam which in turn drives said pin in a reciprocating movement, said pin is disengageable from said inner probe tube for removal of said inner probe tube from said morcellation device.

29. The morcellation device as recited in claim 27, wherein said motor assembly has a telescope port for inserting a telescope parallel to the inner and outer probe tubes.

30. The morcellation device as recited in claim 29, further comprising:
an irrigation fluid source that provides irrigation fluid into an irrigation line; and
an outer sheath tube defining an irrigation channel in fluid communication with an irrigation port connected to said irrigation line, said outer sheath tube surrounding said telescope and said outer probe tube with an open end adjacent to said outer probe tube distal end for directing the irrigation fluid thereto.

31. The morcellation device as recited in claim 27, further comprising:
a footswitch connected to said motor and connectable to the vacuum source for controlling said motor and the vacuum source, wherein when said footswitch is slightly depressed, the vacuum source is activated to create a low level vacuum in said aspiration channel, and when said footswitch is depressed to a mid-position said motor is activated to drive said inner probe tube in said movement relative to said outer probe tube, wherein as said footswitch is gradually depressed beyond said mid-position, said motor and vacuum source are controlled to gradually increase the motor speed and aspiration channel vacuum.

32. The morcellation device as recited in claim 19, wherein said outer probe tube is tapered down in diameter adjacent said distal end of said outer probe tube.

33. The morcellation device as recited in claim 19, further comprising:
a first fluid port formed in said inner probe tube adjacent said distal end thereof;
a second fluid port formed in said outer probe tube adjacent said distal end thereof, wherein said first and second fluid ports are alternately overlapping and not overlapping each other during said movement of said inner probe tube between said first and second positions for supplying fluid into said aspiration channel when said distal end of said outer tube is positioned in a fluid environment, said first and second fluid ports positioned sufficiently away from said first and second apertures to not manipulate the position of the targeted tissue engaged therewith.

34. A morcellation device for morcellating and removing targeted body tissue from within a patient, comprising:

an elongated outer probe tube defining a first interior channel therein and having a first aperture formed adjacent to a closed distal end of said outer probe tube;

an elongated inner probe tube defining an aspiration channel therein and having a longitudinal axis and an outer surface, a spiral shaped groove is formed in said outer surface, an aspiration port in communication with said aspiration channel is formed in said groove, said inner probe tube being slidably disposed inside said first interior channel and rotatable about its longitudinal axis relative to said outer probe tube, a proximate end of said inner probe tube being connectable to a vacuum source;

said first aperture has a first cutting edge and said groove defining a spiral shaped second cutting edge, said first and second cutting edges passing each other when said inner probe rotates relative to said outer probe tube;

wherein during operation, aspiration caused by a vacuum in said aspiration channel from the vacuum source manipulates the targeted tissue to said first aperture and draws a portion of the targeted tissue into said first aperture and said groove, and the portion of targeted tissue is cut by said first and second cutting edges passing each other when said inner probe tube is rotated relative to said outer probe tube, the cut portion of targeted tissue being drawn along said groove, through said aspiration port and through said aspiration channel.

35. The morcellation device as recited in claim 34, wherein at least a portion of said groove is exposed to said first aperture throughout an entire revolution of said inner probe tube relative to said outer probe tube.

36. The morcellation device as recited in claim 35, wherein said first and second cutting edges are non-parallel to each other.

37. The morcellation device as recited in claim 35, wherein said first cutting edge is arc shaped.

38. The morcellation device as recited in claim 35, wherein said first cutting edge is non-linearly shaped to provide a varying cutting action as said inner tube is rotated.

39. The morcellation device as recited in claim 35, wherein said outer probe tube is tapered down in diameter adjacent said distal end of said outer probe tube.

40. A method for transurethral removal of targeted prostatic tissue from within a patient, comprising the steps of:

inserting a transurethral incisional device through the patient's urethra;

incising off at least one piece of targeted prostatic tissue using the incisional device;

inserting a morcellation probe through the patient's urethra;

morcellating the excised piece of targeted prostatic tissue with the morcellation probe; and aspirating the morcellated prostatic tissue through the morcellation probe and out of the patient.

41. The method of claim 40, further comprising the step of:

pushing the excised piece of targeted prostatic tissue into the bladder of the patient before the morcellation step, wherein said morcellation step is performed by said morcellation probe inside the patient's bladder.

42. The method of claim 41, further comprising the steps of:

retrieving the excised piece of targeted prostatic tissue within the patient's bladder with the morcellation probe; and positioning the retrieved piece of prostatic tissue away from the walls of the patient's bladder before the morcellating step.

43. The method of claim 41, wherein the incisional device includes an electrosurgical cutting loop for performing the incising step.

44. The method of claim 41, wherein the incisional device includes an optical fiber having an input end connected to a laser system that generates an optical output and an output end for delivering the optical output through the patient's urethra to the targeted prostatic tissue, wherein said incising step is performed by said optical output exiting said output end.

45. The method of claim 44, wherein said laser system is one of an erbium laser system, a holmium laser system, an Nd:Yag laser system and a KTP laser system.

46. The method of claim 40, wherein said morcellation probe includes:

an elongated outer probe tube defining a first interior channel therein and having a first aperture formed adjacent to a closed distal end of said outer probe tube;

an elongated inner probe tube defining an aspiration channel therein and having a second aperture formed adjacent to a distal end of said inner probe tube, said inner probe tube being slidably disposed inside said first interior channel, a proximate end of said inner probe tube being connectable to a vacuum source, said inner probe tube movable relative to said outer probe tube between a first position where said first and second apertures at least partially overlap each other, and a second position where said first and second apertures do not overlap each other;

a tissue manipulation port formed in one of said outer probe tube adjacent said first aperture and said inner probe tube adjacent said second aperture, such that said tissue manipulation port at least partially overlaps one of said first and second apertures when said inner probe tube is in said second position; and said first aperture has a first cutting edge and said second aperture has a second cutting edge, said first and second cutting edges passing each other when said inner probe tube moves from said first position to said second position;

wherein during operation, aspiration caused by a vacuum in said aspiration channel from the vacuum source manipulates the targeted tissue to said first aperture and draws a portion of the targeted tissue into said first and second apertures when said inner probe tube is in said first position, and the portion of targeted tissue is cut by said first and second cutting edges passing each other when said inner probe tube moves from said first position to said second position, the cut portion of targeted tissue being drawn into and through said aspiration channel, the tissue manipulation port providing suction from the aspiration channel to hold the target tissue in position while said inner probe tube is in said second position.

47. The method of claim 40, wherein said incising step and said morcellating step are performed substantially simultaneously.

* * * * *